(12) United States Patent
Cavusoglu et al.

(10) Patent No.: US 10,026,015 B2
(45) Date of Patent: Jul. 17, 2018

(54) IMAGING CONTROL TO FACILITATE TRACKING OBJECTS AND/OR PERFORM REAL-TIME INTERVENTION

(71) Applicants: Case Western Reserve University, Cleveland, OH (US); The Cleveland Clinic Foundation, Cleveland, OH (US)

(72) Inventors: Murat Cenk Cavusoglu, Cleveland, OH (US); Mark Renfrew, Cleveland, OH (US); Zhuofu Bai, Cleveland, OH (US); Taoming Liu, Cleveland, OH (US); Nathaniel Lombard Poirot, Cleveland, OH (US); Jeffrey Ustin, Cleveland, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 210 days.

(21) Appl. No.: 14/676,392

(22) Filed: Apr. 1, 2015

(65) Prior Publication Data

US 2015/0279031 A1    Oct. 1, 2015

Related U.S. Application Data

(60) Provisional application No. 61/973,524, filed on Apr. 1, 2014.

(51) Int. Cl.
*G06T 7/00*     (2017.01)
*G06K 9/32*     (2006.01)
(Continued)

(52) U.S. Cl.
CPC ............ *G06K 9/6226* (2013.01); *A61B 90/37* (2016.02); *G06T 7/277* (2017.01); *A61B 6/12* (2013.01);
(Continued)

(58) Field of Classification Search
CPC .......... G06T 7/208; G06T 2207/30021; G06T 2207/30096; G06K 9/6226; G06K 2209/05; A61B 90/37; A61B 6/12; A61B 6/5288
See application file for complete search history.

(56) References Cited

U.S. PATENT DOCUMENTS 6,226,409 B1 *   5/2001   Cham .................. G06K 9/6217
                                                                382/228
6,289,233 B1 *   9/2001   Dumoulin .............. A61B 5/055
                                                                324/309
(Continued)

*Primary Examiner* — Sean Conner
*Assistant Examiner* — Pinalben Patel
(74) *Attorney, Agent, or Firm* — Tarolli, Sundheim, Covell & Tummino LLP

(57) ABSTRACT

A method includes acquiring image data from for a given time step. The image data represents at least one of an instrument and a target within an image space that includes patient anatomy. A given belief of system state is estimated to include an estimate of instrument state and target state determined from corresponding measurement and motion models computed based on the acquired image data and control input parameters for the given time step. An expected belief of system state is estimated for a subsequent time step based on the estimated given belief of system state and based on the measurement models and the motion models computed over a plurality of different control inputs parameters. An information metric is computed for each of the expected beliefs of system state and control input parameters are selected for the subsequent time step based on the computed information metrics.

21 Claims, 12 Drawing Sheets

(51) Int. Cl.
  *G06N 7/00*   (2006.01)
  *G06K 9/62*   (2006.01)
  *A61B 90/00*  (2016.01)
  *G06T 7/277*  (2017.01)
  *A61B 6/12*   (2006.01)
  *A61B 6/00*   (2006.01)

(52) U.S. Cl.
  CPC ........ *A61B 6/5288* (2013.01); *G06K 2209/05* (2013.01); *G06T 2207/30021* (2013.01); *G06T 2207/30096* (2013.01)

(56) References Cited

U.S. PATENT DOCUMENTS

| | | | | |
|---|---|---|---|---|
| 6,353,679 | B1 * | 3/2002 | Cham | G06T 7/277 382/181 |
| 6,590,999 | B1 * | 7/2003 | Comaniciu | G06K 9/32 348/416.1 |
| 7,996,062 | B2 * | 8/2011 | Wacker | G01R 33/286 600/420 |
| 9,002,436 | B2 * | 4/2015 | Wu | A61B 6/12 382/128 |
| 9,129,431 | B2 * | 9/2015 | Maeda | A61B 6/032 |
| 9,305,244 | B2 * | 4/2016 | Mathews | G01S 5/16 |
| 9,579,088 | B2 * | 2/2017 | Farritor | A61B 17/00234 |
| 2002/0077546 | A1 * | 6/2002 | Aldefeld | A61B 5/055 600/424 |
| 2003/0053659 | A1 * | 3/2003 | Pavlidis | G06K 9/00335 382/103 |
| 2003/0109780 | A1 * | 6/2003 | Coste-Maniere | B25J 9/1671 600/407 |
| 2003/0176786 | A1 * | 9/2003 | Maschke | A61M 25/0127 600/435 |
| 2004/0044279 | A1 * | 3/2004 | Lewin | G01R 33/4833 600/407 |
| 2006/0293557 | A1 * | 12/2006 | Chuanggui | A61B 90/36 600/101 |
| 2008/0221439 | A1 * | 9/2008 | Iddan | A61B 6/5217 600/424 |
| 2009/0000626 | A1 * | 1/2009 | Quaid | A61N 1/372 128/898 |
| 2009/0264736 | A1 * | 10/2009 | Griswold | A61B 5/055 600/423 |
| 2011/0064290 | A1 * | 3/2011 | Punithakumar | G06K 9/6207 382/131 |
| 2011/0295108 | A1 * | 12/2011 | Cox | A61B 5/042 600/424 |
| 2012/0148102 | A1 * | 6/2012 | Moriguchi | G06T 7/208 382/103 |
| 2013/0303878 | A1 * | 11/2013 | Nevo | A61B 5/062 600/409 |
| 2014/0357953 | A1 * | 12/2014 | Roelle | A61B 1/00006 600/118 |
| 2015/0320514 | A1 * | 11/2015 | Ahn | A61B 34/20 606/130 |
| 2016/0120609 | A1 * | 5/2016 | Jacobsen | A61B 5/062 600/424 |
| 2016/0166345 | A1 * | 6/2016 | Kumar | A61B 34/37 606/130 |
| 2016/0199147 | A1 * | 7/2016 | Shin | A61B 90/37 600/411 |
| 2016/0206389 | A1 * | 7/2016 | Miller | B25J 9/1676 |
| 2016/0302871 | A1 * | 10/2016 | Gregerson | A61B 34/20 |
| 2016/0302925 | A1 * | 10/2016 | Keogh | A61F 2/2433 |
| 2016/0350938 | A1 * | 12/2016 | Maltese | G06T 7/208 |
| 2017/0224427 | A1 * | 8/2017 | Lavallee | A61B 34/20 |
| 2017/0258529 | A1 * | 9/2017 | Winne | A61B 90/20 |

* cited by examiner

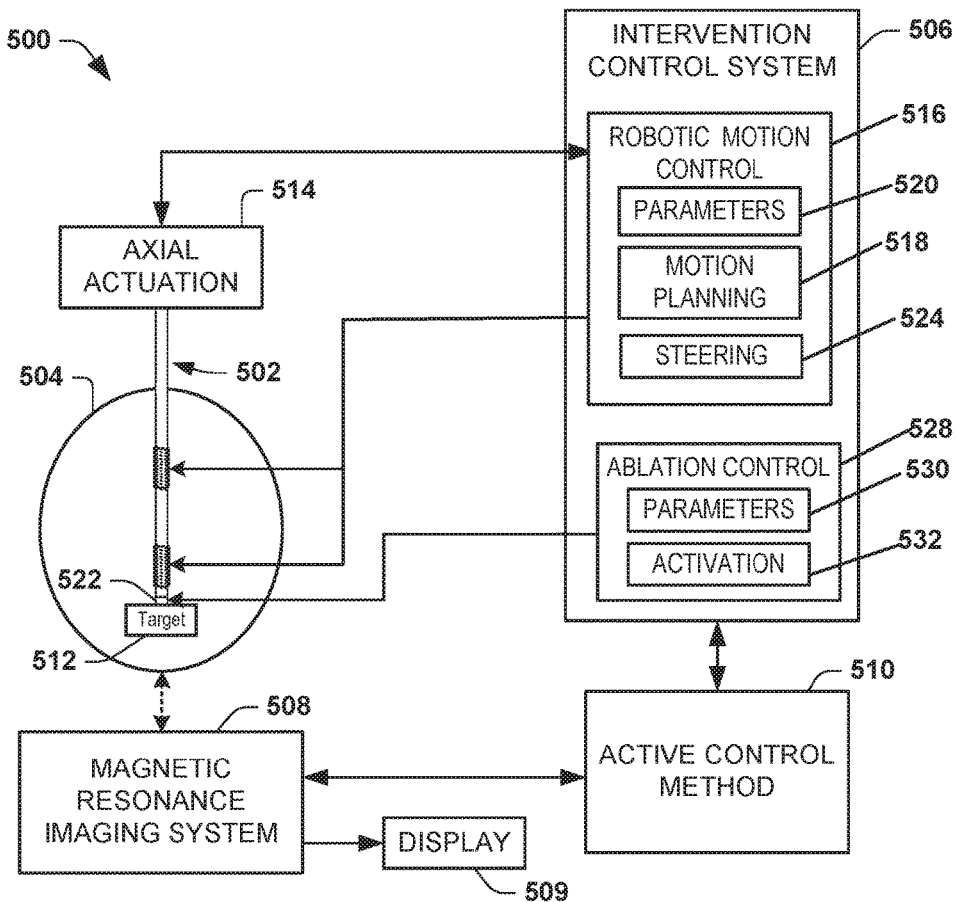
FIG. 20
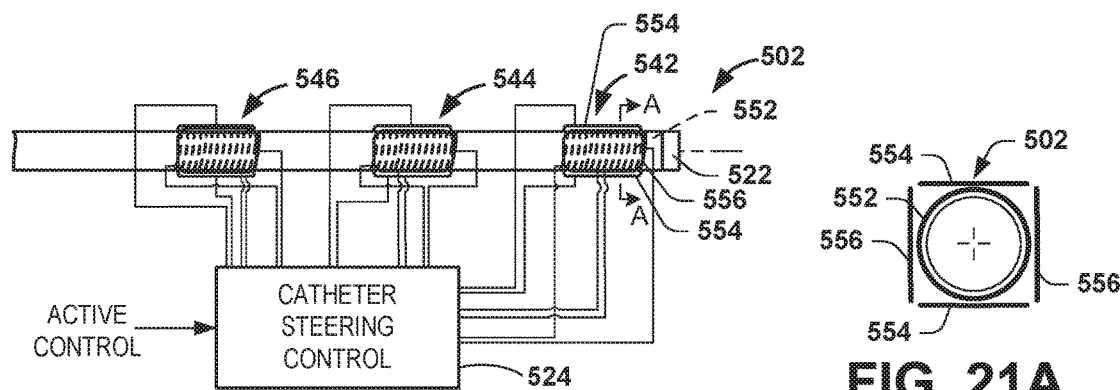
FIG. 21
FIG. 21A

IMAGING CONTROL TO FACILITATE TRACKING OBJECTS AND/OR PERFORM REAL-TIME INTERVENTION

CROSS REFERENCE TO RELATED APPLICATION

This application claims the benefit of U.S. Provisional Patent Application No. 61/973,524, filed Apr. 1, 2014, and entitled PARTICLE FILTER BASED ACTIVE LOCALIZATION OF TARGET AND NEEDLE IN PROBIOTIC IMAGE-GUIDED INTERVENTION SYSTEMS, which is incorporated herein by reference in its entirety.

GOVERNMENT INTEREST

This invention was made with government support under Grant Nos. IIS-0805495, IIS-0905344 and CNS-1035602 awarded by the National Science Foundation and grant Nos. R21 HL096941 and R01 EB018108 awarded by the National Institute of Health. The United States government has certain rights to the invention.

TECHNICAL FIELD

This disclosure relates to imaging control to facilitate tracking objects and/or perform real-time intervention.

BACKGROUND

Physicians commonly perform device insertion procedures for diagnostic or interventional purposes, such as tissue biopsy or drug delivery. As one example, a needle or is inserted in such a way that the needle tip intersects a target of interest (e.g., a tumor). As another example, a catheter can be inserted into the heart to deliver a therapy (e.g., ablation) to heart tissue. These procedures are complicated by the fact that devices are subject to bending while inside the tissue and that the target may move, due either to physiological motions, such as breathing, or due to tissue deformations resulting from the device-tissue interaction. To mitigate problems caused by the uncertainty of the target position and the device configuration, intra-operative medical imaging techniques, such as X-ray fluoroscopy, ultrasound, computerized tomography, and magnetic resonance imaging, can be used to provide real-time information about the device and target locations, and thus allow the device (e.g., needle, catheter or the like) to be steered.

SUMMARY

This disclosure relates to imaging control to facilitate tracking objects and/or perform real-time intervention.

As one example, a method includes acquiring image data from an image system for a given time step. The image data represents at least one of an instrument and a target within an image space that includes patient anatomy, the imaging system and an intervention system operating according to control input parameters. A given belief of system state is estimated for the given time step to include an estimate of instrument state and target state determined from corresponding measurement and motion models computed based on the acquired image data and control input parameters for the given time step. An expected belief of system state is estimated for a subsequent time step based on the estimated given belief of system state and based on the measurement models and the motion models computed over a plurality of different control inputs parameters for at least one of the imaging system and the intervention system. An information metric is computed for each of the expected belief of system states estimated for the subsequent time step and control input parameters are selected to control the at least one of the imaging system and the intervention system the for the subsequent time step based on the computed information metrics.

BRIEF DESCRIPTION OF THE DRAWINGS

FIG. 20 depicts an example of a system to perform real-time intervention.

FIG. 21 depicts an example of a therapy delivery system to deliver ablation therapy via a catheter having a plurality of multi-axial coils.

FIG. 21A is a cross-sectional view taken along line A-A of the device of FIG. 21.

DETAILED DESCRIPTION

This disclosure relates to imaging control to facilitate tracking objects and/or perform real-time intervention.

Systems and methods disclosed herein are configured to actively control an intra-operative imaging system, such as to perform active sensing and/or localization. For instance, systems and methods simultaneously localize a target, which is embedded in or includes tissue, and a flexible instrument (e.g., needle, catheter or other device) as it travels toward the target. Probabilistic measurement models account for noise and false detections in the intraoperative medical images. Probabilistic motion models further can account for motion of the target and instrument being tracked via the imaging system. Beliefs of instrument and tissue locations can be estimated probabilistically, such as by using Bayesian filters to track the motions of the needle and target, based on the images obtained from intra-operative imaging systems (e.g., real-time images). An entropy minimization technique is then employed to actively and in substantially real time select control parameters of the intra-operative imaging system (e.g., the position and orientation of the imaging plane, resolution, scan speed, scan duration, scan area, etc.) to actively estimate the configuration of the instrument and tissue. The process can be performed iteratively based on imaging data acquired for each successive time interval to localize the target embedded in tissue and the instrument as it travels toward the target.

The systems and methods disclosed herein thus can be applied to various forms of percutaneous procedures, such as tissue biopsy, therapy delivery and catheter-based procedures (e.g., cardiac ablation). For instance, the instrument system further can be a robotically controlled catheter that is actively controlled according to control parameters determined from active localization of the target tissue and the instrument configuration, such as disclosed herein. As one example, a receding horizon optimal control approach can be implemented to provide active cancellation of the target tissue motions and perturbations on the catheter deflection resulting from non-steady blood flow. Using a probabilistic model of the catheter motion, the probability of successful diagnostic action or treatment of one or more targets tissue can be increased. Additionally, to reduce the computational complexity, the control system can implement adaptive filters to estimate the expected (e.g., upcoming) motion of the instrument and target, which can help reduce uncertainties in system dynamics due to tissue motion and the perturbations on the catheter motion due to non-steady blood flow and tissue motion.

Figure 1:
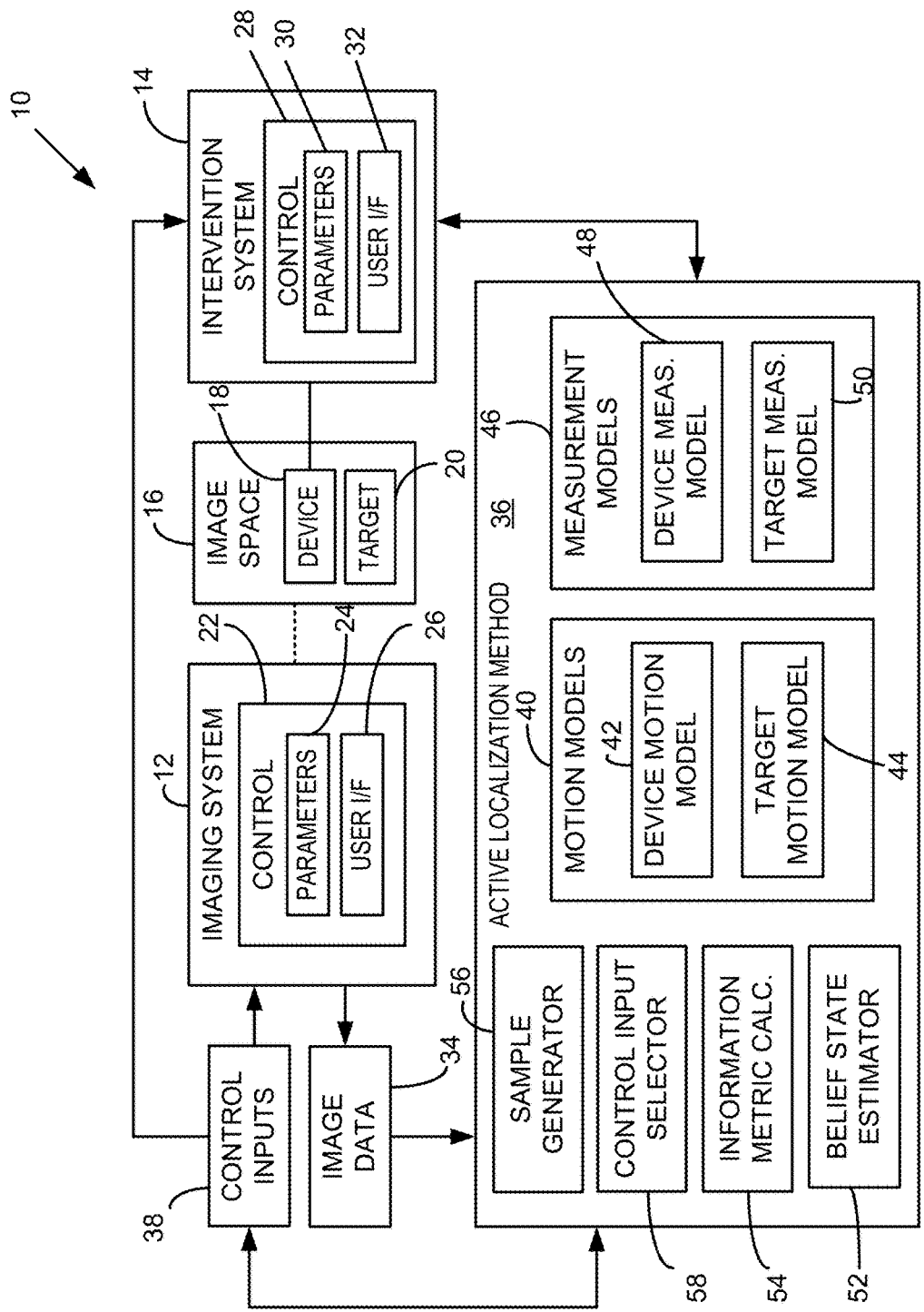
FIG. 1 depicts an example of a system for performing active localization.

FIG. 1 depicts an example of a system 10 to provide for active control of parameters of an imaging system 12 and/or an intervention system 14. The imaging system 12 can be external to the patient's body or internal to the patient's body and configured for intra-operative imaging of an image space 16. As used herein, intra-operative refers to utilizing the imaging during a procedure, such as a diagnostic procedure and/or an interventional procedure that is being performed with respect to the patient's body, which forms at least a portion of the image space 16. The image space 16 includes at least a portion of a patient's body and thus includes a device (e.g., an instrument moveable within the patient's body) 18 and a target 20. The target 20 is a desired location in the image space 16 to which the device 18 is being moved. The target 20, which can be fixed or moveable, further may be an intermediate point along a trajectory or a final destination on such trajectory.

By way of example, the imaging system 12 can be implemented according to various forms of intra-operative medical imaging modalities, including, magnetic resonance, computerized tomography, and ultrasound imaging (and other slice based intra-operative imaging modalities), as well as fluoroscopy (and other projection based intra-operative imaging modalities). The imaging system 12 provides image data 34 that corresponds to a time-based sequence of images of the image space 16, including the target 20 and the device located therein. Changes in the sequence of images provided by the image data 34, for example, can represent movement of the target 20, the device 18 as well as other matter (e.g., surrounding tissue) measurable by the imaging modality employed by the imaging system 12. The imaging data can be provided to a display to visualize the sequence of images acquired over time as well as be stored in memory (e.g., one or more machine readable storage media) for image analysis (e.g. by active localization method 36). The imaging system 12 can include image processing techniques to characterize tissue and other objects (e.g., including device 18 and target 20) in the image space 16, such that image data 34 can include processed images. For a given time step, the image data 34 can be a two-dimensional spatial visualization (e.g., an image across a plane) or three-dimensional spatial visualization (e.g. an image across a volume), and thus the image data can include pixels or voxels, accordingly. The analysis and processing of the images disclosed herein (e.g., by active localization method 36) thus is with respect to the pixels or voxels in the image data 34.

The imaging system 12 includes a control system 22 to control imaging the image space 16 over time (e.g., over one or more imaging time steps). The control system 22 can control the imaging process over time according to a set of time variable input parameters 24. One or more of the input parameters 24, including activation and deactivation of the imaging system 12, can be provided in response to a user input via a user interface 26. The user interface 26 can be a human-machine interface to interact with the imaging system 12, such as to set one or more parameters 24 or otherwise configure the imaging system before or during an imaging procedure.

As mentioned, the intervention system 14 includes a control system 28 to control the intervention system, which can be employed to implement a medical intervention with respect to a portion of the patient's body located in the imaging space 16. The control system 28 can control the intervention system 14, including controlling motion and/or positioning of the device 18, over time according to a set of associated operating parameters 30. The control system 28 also includes a user interface 32 that can be utilized to provide or adjust one or more of the parameters 30 in response to a user input, including activation and deactivation of the intervention system 14. The user interface 32 can include a human-machine interface to interact with the invention system 14, such as to set one or more of the parameters 30 or otherwise configure and/or control the intervention system 14 before and/or during an interventional procedure.

As an example the intervention system 14 is configured to perform a percutaneous therapy with respect to the patient's body. For example, the intervention system 14 includes the device 18 (e.g., a needle, catheter or the like), which device is inserted percutaneously into the patient's body and advanced to the target 20 for performing a respective procedure (e.g., diagnostic and/or treatment of tissue). In some examples, the intervention system 14 can include a specialized instrument, such as robotic tools or instruments, which inserted into the patient and are guided to the target (e.g., a fixed or moving target) 20 based on active localization via intra-operative medical imaging (e.g., via imaging system 12). As one example, the intervention system 14 can be implemented as a robotically controlled catheter ablation system in which the catheter tip (e.g., device 18) is to ablate target tissue 20 based on control parameters 30 that vary with respect to time.

As a further example, the device 18 can be implemented as an elongated catheter having a plurality of a sets of coils at a plurality of spaced apart locations including the proximal distal tip of the catheter and at least another set of catheters spaced a distance axially apart from the catheter tip. The control system 28 generates output signals to control the coil in the device 18 such as input electric current selectively provided to energize respective coils as to cause movement of the catheter toward a desired point on a given trajectory between the end point and the target site. For example, the control 28 can implement the control methods including inverse kinematics and Jacobian controls to adjust the position of the catheter (or other instrument) toward the target 20 based on active control inputs generated by the active localization method 36. In response to the current applied by the intervention system 14, for example, magnetic moments can be generated on each respective coil including the tip or other location where the coils reside along the elongated body portion of the catheter. The magnetic moments generated at each coil sets interact with the magnetic field of the MR scanner implemented at the imaging system 12 to deflect of the flexible elongated body of the catheter in a desired direction with respect to a longitudinal axis thereof (see, e.g., FIG. 21).

As disclosed herein, the system 10 includes the active localization method 36 to generate and actively control one or more control inputs 38 for the system 10. For example, at each time step, the active localization method 36 calculates $u_t$, the image parameters most likely to maximize information gain (IG) about the current state, uses the imaging system to obtain an image, processes the image to get a measurement of the current needle and target location, and updates device and target beliefs bel($n_t$) and bel($g_t$) according to the current measurement $z_t$.

In the example of FIG. 1, the control inputs 38 can provide active control for the imaging system 12 and/or the intervention system 14. The control inputs 38 set one or more of the image parameters 24 of the imaging system 12 determined to maximize information gain about the current state of the system 10. Additionally or alternatively, the control inputs 38 also can set one or more of the control parameters 30 of the intervention system 14 also to maximize information gain for the system 10. The control parameters 30 set via the control inputs 38 can be employed to steer and adjust the position of the device (e.g., catheter or needle) in substantially real time. The control inputs 38 to the intervention system 14 thus can be utilized to navigate a tip of the device to the target site 20 in the patient's body as well as to implement relative motion control (e.g., motion cancellation) once at the target site so that the device 18 moves commensurately with movement of the tissue target (e.g., to maintain continuous contact).

In the example of FIG. 1, the active localization method 36 includes one or more probabilistic motion model functions 40, including a device motion model 42 and a target motion model 44. The device motion model 42 is programmed to compute a probability density function for the instrument to represent uncertainty in estimating the motion of the device (e.g., needle, catheter or other intra-operative device). For instance, the device motion model 42 represents motion of the device 18 over time by specifying a state transition probability density function for the device. The target motion model 42 is similarly configured to represent motion of the target over time by specifying a state transition probability density function for the target. Thus, the target motion model can be programmed to compute a probability density function for the target to represent uncertainty in estimating the motions of the target. The motion of the tissue and the device can be modeled either deterministically or stochastically.

As one example, the target is assumed to be a spherical object, with radius R, undergoing Brownian random motion to account for the displacements of the target as a result of unmodeled tissue deformations. The state of the target at time t consists of the spatial coordinates (e.g., x, y, z) of the center of the target, and will be denoted as $x_{g,t}$. Then each coordinate of the state of the target at time t+Δt can be obtained from a Gaussian probability density function, such as follows:

$$p(x_{g,t+\Delta t}|x_{g,t}) = \mathcal{N}(x_{g,t+\Delta t}; x_{g,t}, K\Delta_t) \qquad (1)$$

where k is the variance of the Brownian motion for unit time, and $\mathcal{N}(\bullet; \mu, \sigma^2)$ is the normal distribution function with mean $\mu$ and variance $\sigma^2$.

In the following example, the device motion model 42 for device 18 is described as modeling a flexible needle is inserted into a relatively stiff insertion medium that is assumed to be relatively stiff, although different types of devices and insertion media can be utilized in different types of interventions, as disclosed herein. In this example, the needle device will therefore deform while it is being inserted. The needle can be modeled kinematically as a piecewise cubic spline model. At time t, the shape of the needle is given by the parametric equation $$\gamma(\lambda)_{j,t} = a_{j,t} + b_{j,t}\lambda + c_{j,t}\lambda^2 + d_{j,t}\lambda^3, \qquad (2)$$
$$j = 0 \ldots K-1, 0 \le \lambda \le 1,$$

where $a_{j,t}, b_{j,t}, c_{j,t}, d_{j,t} \in R^3$ are the coefficients of the spline segment j at time t, K is the number of segments, and is the parameter of the spline.

The continuity of the needle curve and its tangent direction is enforced by the boundary conditions $$\gamma(1)_{j,t} = \gamma(0)_{j+1,t} \qquad (3)$$

$$\frac{\gamma'(1)_{j,t}}{\|\gamma'(1)_{j,t}\|} = \frac{\gamma'(0)_{j+1,t}}{\|\gamma'(0)_{j+1,t}\|} \qquad (4)$$

for j=1 ... (K−1), i.e., the last point of a spline is the first point of the next spline, and the tangents of the lines are equal at that point. The state of the needle at time t, denoted by can then be defined by the x; y; z coordinates and tangents at the endpoints of the spline segments, subject to the continuity conditions of Eqs. 3-4.

Because there is no closed-form solution to generate a cubic spline from a set of starting conditions, the cubic splines are initially generated from quadratic splines $\gamma(\lambda)_{j,t} = a_{j,t} + b_{j,t}\lambda + c_{j,t}\lambda^2$, which can be generated by the following method. For simplicity, let $p_0 = \gamma(0)_{j,t}$ be the starting point of spline j at time t, $t_0 = \gamma'(0)_{j,t}$ be the tangent at $p_0$, $p_1 = \gamma(1)_{j,t}$ be the endpoint of the spline, $p_1 = \gamma'(1)_{j,t}$ be the tangent at $p_1$, and l>0 be the length of the spline, with $p_0$; $t_0$; $t_1 \in R^3$, $1>0 \in R$. Then a spline satisfying these constraints can be found as follows.

First the magnitude of the angle $\theta_s$ between the starting tangent $t_0$ and the ending tangent t1 is found:

$$t_{Sn} = \frac{t_0}{\|t_0\|}$$

$$t_{En} = \frac{t_1}{\|t_1\|}$$

$$n_p = t_{0n} \times t_{0n}$$

$$\theta_s = \|n_p\|.$$

If $\theta_s < \varepsilon$ for some error value $\varepsilon$, then the tangents are considered to be coplanar, and the result is a quadratic spline (i.e., a straight line) with the following parameters:

$$a = P_0$$

$$b = lT_{0n}$$

$$c = [0 0 O]^T$$

Otherwise, the tangents are not coplanar, and the spline parameters are found as follows. First, the matrix is found which describes the relationship between the world coordinate frame and the local spline frame, RWL.

$$n = \frac{n_p}{\theta_s}$$

$$u = \frac{t_{0n} + t_{1n}}{\|t_{0n} + t_{1n}\|}$$

$$v = n \times u$$

$$R_{WL} = [u \ v \ n]$$

Then the parameters in the local coordinate frame are found:

$$\theta_c = t_{1n}^T t_{1n}$$

$$\theta = \frac{a\tan2(\theta_s, \theta_c)}{2}$$

$$d = \frac{2l}{a\sinh(\tan\theta\cot\theta + \sec\theta)}$$

$$ABC_L = \begin{bmatrix} 0 & d & 0 \\ 0 & d\tan\theta & -d\tan\theta \\ 0 & 0 & 0 \end{bmatrix}$$

And finally, the final spline parameters are found as follows:

$$[a \ b \ c] = R_{WL}[a \ b \ c]_L + \begin{bmatrix} 0 & 0 \\ p_S & 0 & 0 \\ 0 & 0 \end{bmatrix} \quad (5)$$

The quadratic splines are then converted into cubic splines simply by adding a fourth term $d\lambda^3$ and setting the parameter d to zero. The needle control input, $u_{n,t}$, can include device motion parameters that represent the displacement of the entry point, the change in the tangent direction at the entry point, and the insertion length. Here, the incremental motion of the needle as it is inserted into the tissue is modeled purely kinematically (i.e., without explicitly calculating estimating the needle tissue interaction forces) as a random process to account for uncertainties in the needle motion and deflection. Because, in some examples, the active localization method 36 can include a belief state estimation method 52 based on Bayesian filtering using particle or Kalman filters, it is sufficient in such examples to sample from the motion model $p(x_{n,t}|u_{n,t}, x_{n,t-1})$, instead of computing the posterior probability density function for arbitrary states and inputs.

Given the needle control input $u_t$, the motion of needle is modeled as three distinct motion phases. The first phase is the change in the needle configuration as a result of the motion of the needle base, i.e., the displacement of the entry point of the needle into the tissue and the change of its tangent direction. The second phase is the axial insertion of the needle into the tissue. The third phase is the addition of random perturbations to the shape of the needle due to various unmodeled tissue-needle interaction forces (e.g., friction, tissue deformation, etc.), which modify the state of the needle by perturbing the positions and tangents of the control points.

During the first phase propagation of an insertion point is accomplished in two steps. In the first step, the insertion point is perturbed and the perturbation is propagated through the spline array under the assumption that the needle is rigid. For each spline in the array $S_i$, i=0 . . . K−1, with parameters [a b c d], initial starting point $p_0$, initial starting tangent $t_0$, $t'_0$, initial endpoint $p_1$, and initial ending tangent $t_1$, let q be the translational perturbation of the starting point and u be the rotational perturbation. Then the new starting point and tangent are $$p'_0 = p_0 + q$$

$$t'_0 = t_0 + u$$

and the endpoint and ending tangent can be expressed as:

$$p_1' = p_0 + q(p_1 - p_0) + q$$

$$t_1' = t_0 + u$$

The four parameters [a' b' c' d'] of the new cubic spline are then given by the following.

$$\rho = \|t_0\| \quad (6)$$

$$\mu = \|t_1\|$$

$$t_{0x} = \rho \frac{t'_0}{\|t'_0\|}$$

$$t_{1x} = \mu \frac{t'_1}{\|t'_1\|}$$

-continued $$[a'\ b'\ c'\ d'] = \begin{bmatrix} p'_0 \\ t'_{0x} \\ -3p_0 + 3p_1 - 2t_{0x} - t_{1x} \\ 2p_0 - 2p_1 + t_{0x} + t_{1x} \end{bmatrix}^T$$

Finally, the parameters [a' b' c' d'] of the old spline $S_i$ are mixed with the parameters [a b c d] of the new spline $S'_i$ to obtain the final spline. Let $l_0$ and $l_1$ be the length of $S_i$ and $S'_i$, w be a weight parameter, and $d_i$ be the distance along the spline array of the initial point of $S'_i$. For $l = \min(l_0, l_1)$, let $p_0$ and $p_1$ be vectors of points along the splines $S_i$ and $S'_i$ at the distance $$\frac{l}{10}, \frac{2l}{10}, \dots \frac{9l}{10}.$$

Then the ρ-μ parameterization for the new spline can be found as follows.

$$v_w = \begin{bmatrix} w^{\frac{l}{10}} & w^{\frac{2l}{10}} & \dots & w^{\frac{9l}{10}} \end{bmatrix}$$

$$M_w = [v_w^T\ v_w^T\ v_w^T]$$

$$p_w = M_w p_0 + (1 - M_w)p_1$$

$$w_0 = w^{d_0}$$

$$w_1 = w^{d_0 + l}$$

$$\hat{p}_0 = w_0 p_0 + p'_0(1 - w_0)$$

$$\hat{t}_0 = w_0 \frac{t_0}{\|t_0\|} + \frac{t'_0}{\|t'_0\|}(1 - w_0)$$

$$\hat{\rho} = w_0 \|t_0\| + \|t_1\|(1 - w_0)$$

$$\hat{p}_1 = w_1 p_1 + p'_1(1 - w_1)$$

$$\hat{t}_1 = w_1 \frac{t_1}{\|t_1\|} + \frac{t'_1}{\|t'_1\|}(1 - w_1)$$

$$\hat{\mu} = w_1 \|t_1\| + \|t_1\|(1 - w_1)$$

The new spline's Cartesian parameters are then generated from the $\hat{\rho}$ and $\hat{\mu}$ by the method in Equation 6. The new endpoint of spline S0 i then becomes the new starting point of spline $S'_{i+1}$ and the process is repeated iteratively for each spline $S'_i$, i=0 . . . K−1, where K is the number of splines.

Following propagation of the insertion point, the needle is inserted axially by some distance d. This proceeds as follows. First, the tangent $t_e$ at the needletip $p_e$ is randomly perturbed to obtain a new needle tip direction $t_n$. A new quadratic spline $S_n$ with minimum curvature is then found by the method in phase 1 which satisfies the conditions starting point $p_e$, starting tangent $t_e$, ending tangent $t_n$, and length d. This new spline is then combined with the $S_e$, and the spline array is recalculated, with the first or last splines being split into respective halves if their lengths exceed a maximum spline length parameter.

The device motion model 42 further can be generated to account for random perturbations that may occur intraoperatively. For example, each spline Si, i=1::K in the spline array is assumed to be perturbed randomly. The starting and endpoints and tangent of $S_0$ are perturbed and the spline parameters are recalculated. The new endpoint is then propagated to $S_1$ and the process is repeated for each spline in the array.

Figure 13:
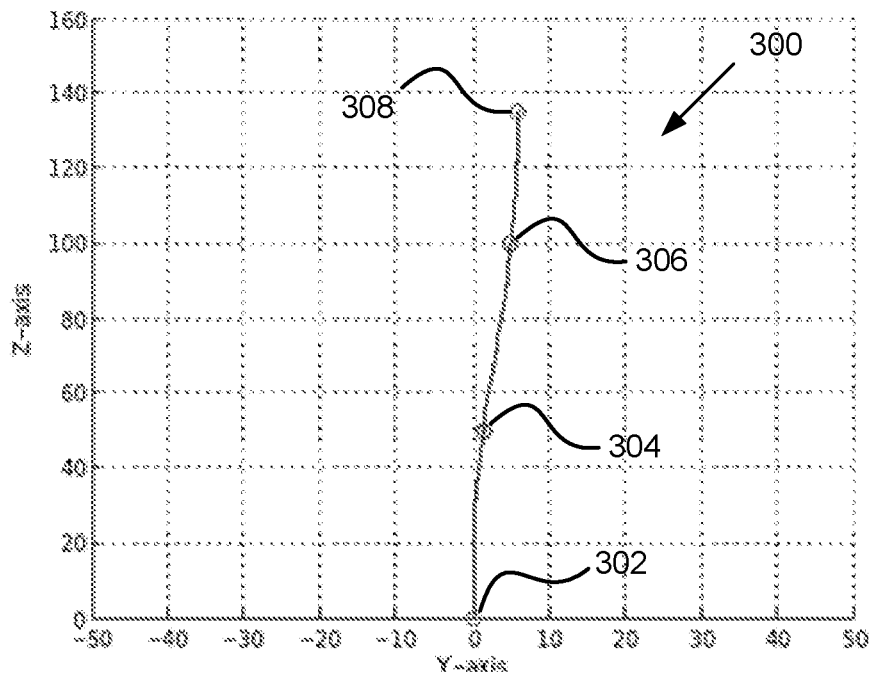
FIG. 13 depicts an example of a four control point instrument configuration being inserted into simulated tissue according to an instrument motion model.
Figure 14:
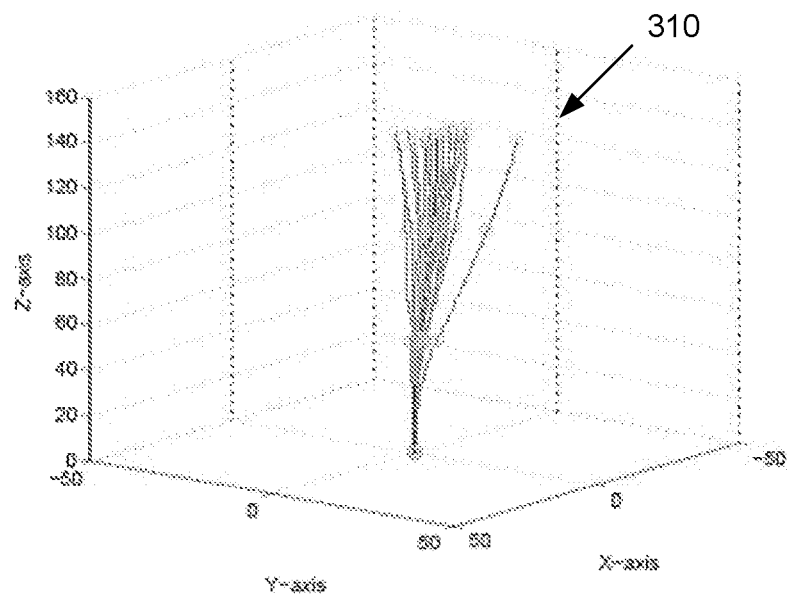
FIG. 14 depicts examples of sample instrument configurations from a posterior distribution according to the instrument motion model of FIG. 13.

A sample generation function 56 is programmed to generate random samples for the device model to account for random perturbations of the device. For example, the sample generator 56 can generate random samples from $p(x_{n,t}|u_{n,t}, x_{n,t-1})$, for a given prior state $x_{n,t-1}$ and device control input $u_{n,t}$. The sample generation function 56 can perturb the commanded control parameters, including the displacement of entry port, rotation of the tangent direction, insertion length, and rotation of the device tip insertion direction. For example, the sample generation function 56 calculates the device (e.g., needle or catheter) configuration as a result of the base motion and then calculates the configuration after its insertion. The sample generation function 56 additionally perturbs the final device configuration by randomly perturbing the positions and tangents of the control points of the model. Examples of needle insertion simulations are shown in FIGS. 13 and 14.

Returning to FIG. 1, the active localization method can also utilize one or more measurement models 46. In the example of FIG. 1, the measurement models 46 include a device measurement model 48 and a target measurement model 50. The measurement models can provide probabilistic models of the medical imaging system 12 and the associated image processing algorithms programmed to account for noise and false detections in the intra-operative images (e.g., image data 34). The measurement model system 46 thus explicitly model inherent uncertainty in the sensor measurements implemented by the imaging system 12.

In the following examples, the sensor measurement can correspond to image data acquired by the imaging system 12 at a given time. The measurement model thus can be represented as a conditional probability distribution function $p(z_t|x_t)$, where the distribution represents a probability of the measurement vector at times t given the system state $x_t$. In this example, $x_t$ represents the system state and includes locations of the device 18 and the target 20 within the image space 16 as well as the current image parameters $u_t$, and $z_t$ represents the measurement vector.

The measurement models 46 can include a device measurement model 48 and a target measurement model. The device measurement model 48 can represent whether the device has been detected in the current image as well as indicate the location of the detected device on the current image parameters. The target measurement model 48 can similarly represent whether the target has been detected for the current image parameters as well as indicate the location of the detected target in a corresponding image plane.

By way of example, the image processing corresponding to the measurement models 46 that is performed on the intra-operative medical image data is treated as a black-box system, whose output is two logical variables, $z_{nd,t}$ and $z_{td,t}$, which indicate, respectively, whether the needle and target have been detected in the current image. The measurement models 46 can also provide an output including two image coordinate variables, $z_{nc,t}$ and $z_t$, which indicate the locations of the detected needle and target on the image plane. As a result of the outputs being used for estimating beliefs for system state, the measurement models 46 can be adapted or modified with little affect on associated system operation. Since the measurements of the device and target can be assumed to be independent, the probability distribution function can be expressed as the product of respected distributed function for the device and the target, namely $p(z_t|x_t) = p(z_{n,t}|x_t)p(z_{g,t}|x_t)$. For notational simplicity, the measurement outputs for detection and location the needle and target are denoted by $z_{n,t}$ and $z_{g,t}$, respectively.

As a further example, the device measurement model using the intraoperative imaging system incorporates multiple types of needle detection errors, such as false positives and misses, as well as error in image locations of correctly detected needle. In a noise free sensor, the needle would be detectable in an image if the needle intersects the current image plane, and the intersection point on the image plane would be the corresponding image coordinates of the detected needle. The visibility of the needle in the ideal noise-free image will be denoted by the logical variable. $I_n$, where a true value corresponds to an actual intersection between the needle and the image plane, and the corresponding image coordinates will be denoted by $p_n$.

In the actual (noisy) imaging system, the needle imaging is assumed to have true positive and false positive rates of $\alpha_{n,tp}$ and $\alpha_{n,fp}$, respectively. Then, the true and false positive probabilities can be written as:

$$p(TP|x_t) = \begin{cases} \text{if } I_n = \text{true}: & \alpha_{n,tp} \\ \text{if } I_n = \text{false}: & 0 \end{cases}, \quad (7)$$

$$p(FP|x_t) = \begin{cases} \text{if } I_n = \text{true}: & (1-\alpha_{n,tp})\alpha_{n,fp} \\ \text{if } I_n = \text{false}: & \alpha_{n,fp} \end{cases}.$$

Adding the true and false positive rates yield the needle detection probability:

$$p(z_{nd,t} = \text{true}|x_t) = \tag{8}$$
$$p(TP|x_t) + p(FP|x_t) = \begin{cases} \text{if } I_n = \text{true}: & \alpha_{n,tp} + (1-\alpha_{n,tp})\alpha_{n,fp} \\ \text{if } I_n = \text{false}: & \alpha_{n,fp} \end{cases},$$

and $$p(z_{nd,t} = \text{false}|x_t) = 1 - p(z_{nd,t} = \text{true}|x_t). \tag{9}$$

For a true positive (TP), the measured needle location in the actual (noisy) imaging system is assumed to have zero-mean Gaussian noise. For a false positive (FP), the measured locations is assumed to be uniformly distributed over the image plane. Then, for each of the two coordinates i=1, 2 on the image, $$p(z_{nc,t}^i|TP,x_t) = \mathcal{N}(z_{nc,t}^i; p_n^i, \sigma_{n,i}^2), \tag{10}$$

$$p(z_{nc,t}^i|FP,x_t) = \mathcal{U}(z_{nc,t}^i; \min_i, \max_i), \tag{11}$$

where $\min_i$, $\max_i$ is the minimum and maximum coordinates of the image plane in the corresponding dimension, and U(___; min; max) is the uniform distribution function in the domain [min, max]. Combining the probability density functions for the needle detection and coordinates, using the conditional probability and total probability equations, yields the probability density function of the needle measurement model as:

$$p(z_{nd,t}, z_{nc,t}^1, z_{nc,t}^2|x_t) = p(z_{nc,t}^1, z_{nc,t}^2|z_{nd,t}, x_t)p(z_{nd,t}|x_t) = \tag{12}$$
$$p(z_{nc,t}^1, z_{nc,t}^2|TP, x_t)p(TP|x_t) + p(z_{nc,t}^1, z_{nc,t}^2|FP, x_t)p(FP|x_t) =$$
$$p(z_{nc,t}^1|TP, x_t)p(TP|x_t)p(z_{nc,t}^2|TP, x_t)p(TP|x_t) +$$
$$p(z_{nc,t}^1|FP, x_t)p(FP|x_t)p(z_{nc,t}^2|FP, x_t)p(FP|x_t),$$

where, in the last step, the independence of the measured needle location's noise in the two dimensions is used.

In the derivations for the device measurement model provided above, the dependence of the needle measurement to the configuration of the imaging plane has not been explicitly included in the equations to simplify the notation. The derivations could, of course, be extended to account for such dependence.

The target measurement model is similar to the needle measurement model described above, with one difference. In the target measurement model, there is a true positive probability value that is a function of the target's cross sectional area visible in the image plane instead of a constant true positive rate. For example, the true positive detection probability is defined as:

$$p_{tp}(x_t) = \begin{cases} A_g \geq A_o: A/A_o \\ A_g \geq A_o: 1 \end{cases} \tag{13}$$

where $A_g$ is the target's cross section area visible in the image plane, and $A_0$ is a critical area above which the detection probability is equal to 1. Then the true and false positive probabilities for target detection can be written as:

$$p(TP|x_t) = \begin{cases} \text{if } I_g = \text{true}: & p_{tp}(x_t) \\ \text{if } I_g = \text{false}: & 0 \end{cases}, \tag{14}$$

$$p(FP|x_t) = \begin{cases} \text{if } I_n = \text{true}: & (1-p_{tp}(x_t))\alpha_{g,fp} \\ \text{if } I_n = \text{false}: & \alpha_{g,fp} \end{cases},$$

where the variables are defined analogously to the needle model case. The remaining equations of the target measurement model are similar to the needle measurement Eqs. 8-12, with the relevant variables defined in an analogous way, and will not be repeated. Similar to the needle measurement model equations, the dependence of the target measurement on the configuration of the imaging plane has not been explicitly included in the equations in order to simplify the notation.

Belief state estimator 52 is programmed to employ the motion models 40 and measurement models 46 to probabilistically estimate the current state of the system 10. For example, the belief state estimator 52 can employ Bayesian filters to estimate the posterior probability to provide a corresponding belief associated with the state of the system. As an example, the belief state estimator 52 can estimate the belief of the system state at each respective time step t, t+1 . . . . In some examples, the belief state estimator 52 can provide the estimate of system state by computing a first belief estimate of the device state at time t and another estimate to represent the belief of the target state at time t. In other examples, the belief state estimator 52 can compute an aggregate state of the system at each time t.

The belief state estimator 52 can also be utilized to compute an expected belief at a future time step (e.g., t+1, where t is the current time step) based on the belief estimate for the current time t (e.g., the belief of the device state bel($n_t$) and the belief of the target state at time t bel($g_t$)) over a corresponding range of input control parameters 38. For instance, the active localization method 36 includes a control input selector 58 to actively select values for one or more of the control inputs to maximize information about the state of the system. The information about the state of the system 10 can be determined by an information metric calculator 54. The information metric calculator 54 can compute the information metric based on the estimate future beliefs of system state, and the active localization method 36 can employ the control input selector 58 to select the set of control inputs 38 that maximizes the information metric for the next (e.g., future) time step. As mentioned, the control inputs 38 can include one or more control parameters for controlling operation of the imaging system 12 and/or the intervention system 14.

As an example, the information metric calculator 54 can determine the information metric by calculating the entropy of the estimated future belief states (e.g., device belief states and target belief states). As an example, the active localization method 36 can employ a greedy algorithm based on entropy minimization to enable the control input selector 58 to select a set of control inputs 38 to maximize the expected information gain, corresponding to a minimization of the computed system entropy. In some examples, the intervention control system 28 can implement a separate motion planner in control similar to the control input selection implemented by the active localization method 36 to determine a set of corresponding parameters 30 based on the current belief on the state of the device 18 and the current belief of the state of the target 20. In other examples, the active localization method 36 can further be programmed to ascertain control input that includes one or more of the intervention control parameters to determine the device control inputs.

By way of further example, the active localization method 36 can provide the control inputs 38 to control the imaging system to actively localize a tip (or other structural component) of the device 18 and a centroid of the target 20. During such active localization control, the intervention control system 28 can employ its control input parameters to execute one or more interventional tasks. As disclosed herein, the interventional task can include directing the needle towards the target via axial insertion of the instrument and/or to selectively activate one or more coils disposed along the length of the instrument, as disclosed herein, to deflect the distal end portion in a direction toward a desired trajectory to the target location.

Additionally or alternatively, the interventional task can include a combination of interventions, such as including applying a therapy to the target site. The target site may be fixed for moveable relative to the delivery mechanism located on the device 18 and the control input parameters can be utilized to implement movement of the distal end of the device to maintain contact at the target site (e.g., patient tissue). Examples of therapies that can be applied to one or more target tissue sites include ablation (e.g., RF ablation, cryoablation, microwave ablation, laser ablation, surgical ablation or the like), electrical stimulation of tissue (e.g., muscle tissue or nervous tissue), delivery of chemicals or other types of therapy that can be delivered percutaneously. One or more of the control parameters of the intervention control system 28 can be established by or be derived from the control inputs generated by the active localization method 36, as disclosed herein, to implement each interventional task.

Figure 2:
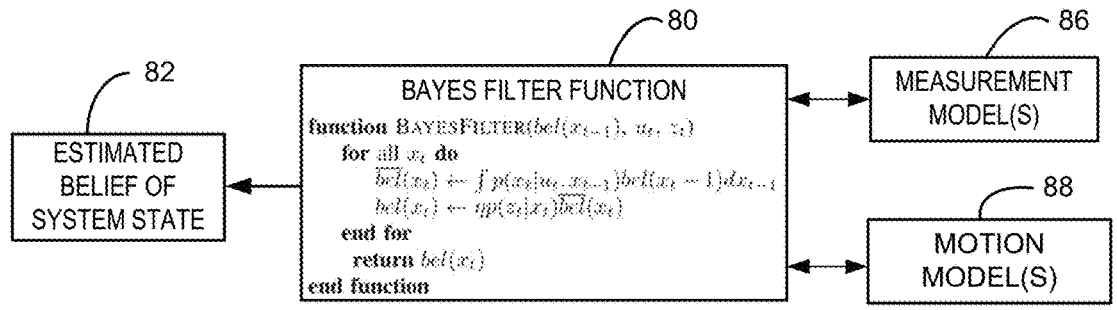
FIG. 2 depicts an example of a belief estimation function that can be utilized in an active localization system.

FIG. 2 depicts an example of a Bayes filter function 80 (e.g., corresponding to belief state estimator 52 or FIG. 1) that provides an estimated belief of system state 82 that can be utilized in the active localization method disclosed herein (e.g., active localization 36 of FIG. 1). The Bayes filter function 80 employs one or more measurement models 86 and one or more motion models 88 (e.g., models 40 and 46 of FIG. 1) to represent motion of the device and target in the computations. The filter function 80 can provide the estimated belief of system state 82 as the current state of the system 10 including the state of the device 18 and state of the target 20, as disclosed herein.

For example, at each time step corresponding image data and current state parameters are obtained and utilized by the estimator 80. The Bayesian filter function 80 tracks the device (device 18) and target (target 20) at each time step by storing hypotheses regarding their states. Example implementations of Bayesian filters that can be used include the unscented Kalman filter (UKF) and the particle filter (PF). At each timestep t, the filter function 80 updates its belief $bel(x_t)$ of the state $x_t$. The hypotheses are represented using the motion models 88, which, when given a current state of the needle and target, specify the state transition probability density functions for their next state. The state transition probability density functions are used in the prediction step of the Bayesian filter function 80.

For example, as demonstrated by pseudo code in the filter function block 80, the belief $bel(x_t)$ can be computed in two steps. First, the Bayes filter function 80 calculates the probability distribution for the current state based on the previous state and the current control $u_t$ to provide a provisional belief $\overline{bel}(x_t)$. Next, the filter function 80 multiplies the provisional belief by the probability of the observation of the current measurement $z_t$, as shown to provide the corresponding estimated belief $bel(x_t)$ of the system state 82. Examples of Bayesian filters that can be implemented as the Bayes filter function 80 include the particle filter function (see, e.g., FIG. 3) and the unscented Kalman filter (UKF) function (see, e.g., FIG. 4).

Figure 3:
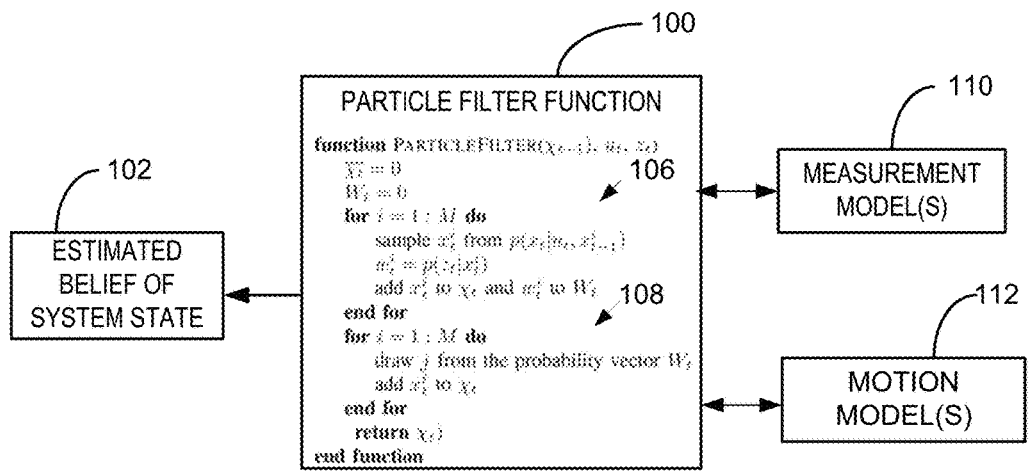
FIG. 3 depicts another example of a belief estimation function that can be utilized in an active localization system.

FIG. 3 depicts an example of a particle filter function 100 that can provide corresponding estimated beliefs of system state 102. In the example of FIG. 3, the particle filter function 100, similar to the Bayesian filter function 80, employs one or more measurement models 110 and one or more motion models 112, such as disclosed herein (e.g., models 40 and 46). The particle filter function 100 provides the estimated belief of system state as a set of particles that represent possible state of the target and device based on a previous estimate of system state. For instance, the particle filter function 100 can provide the posterior belief, corresponding to the estimated belief of system state 102, as a set of random samples drawn from the posterior. The distribution of the set of particles approximates the posterior belief $bel(x_t)$. As mentioned, the particle filter function 100 constructs its current particle set $X_t$ from its previous estimate $X_{t-1}$, current control input $u_t$ and the current measurement $z_t$.

As an example, pseudo code to implement the particle filter function 100 is demonstrated in the filter function block of FIG. 3. The particle filter function 100 is a sequential Monte Carlo sampling approach that is a non-parametric implementation of the Bayes filter function 80. The particle filter function 100 in FIG. 3 constructs its current particle set $X_t$ from its previous estimate $X_{t-1}$, a current control input $u_t$, and a measurement $z_t$. Like the Bayes filter function 80, it has two basic components of operation. First, for each particle $x_{i,t-1}$ in the previous particle set $X_{t-1}$, it generates a hypothetical current state $x_{i,t}$ based on the control $u_t$ and the state transition distribution, and the weight with $w^i_t$ of the hypothetical particle. Then, the newly-generated particles are resampled according to their weight, which tends to eliminate particles that are unlikely to be the true state of the system. This helps to reduce the necessary number of particles required to represent the system state as well as the associated computational requirements to produce the estimate belief of system state 102.

Figure 4:
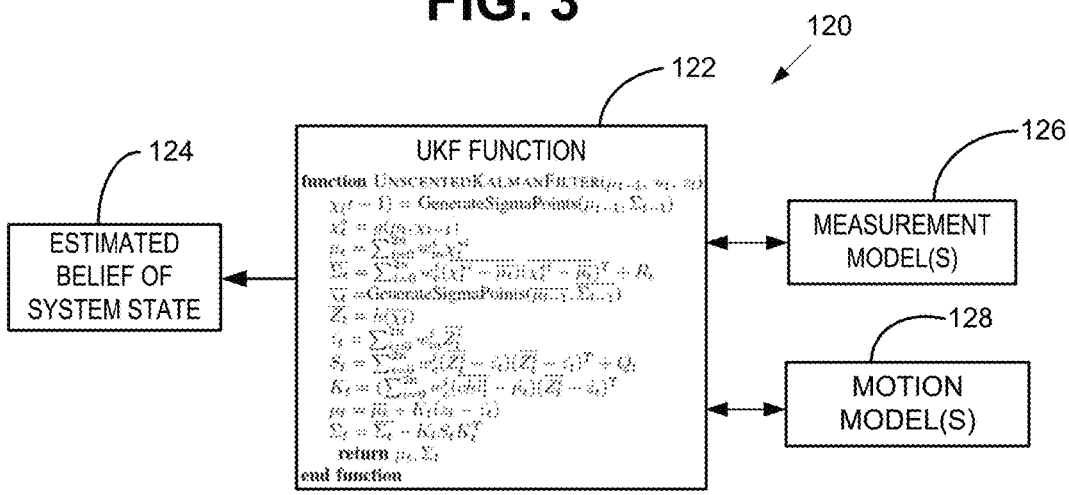
FIG. 4 depicts yet another example of a belief estimation function that can be utilized in an active localization system.

FIG. 4 demonstrates an example of an unscented common filter (UKF) function 120 (e.g., corresponding to the belief state estimator 52) that can generate a corresponding estimated belief of system state 124. Like the particle filter, the UKF function 120 is an implementation of the Bayes filter algorithm. The belief at time t is represented by a mean $\mu_t$ and a covariance matrix $\Sigma_t$, and like the particle filter is updated using a current control input $u_t$ and a measurement $z_t$.

As demonstrated in pseudo code in the UKF function block 120 of FIG. 4, the UKF function utilizes the unscented transform to create a linear approximation of the underlying function by the use of sigma points. These are denoted x and are located at the mean $\mu_t$ and along the principal axes of the covariance matrix $\Sigma_t$ at a symmetric distance from $\mu_t$. Each sigma point $\chi_i$ has two weights associated with it, $w^i_m$ which is used to calculate $\mu_t$, and $w^i_c$ which is used to calculate $\Sigma_t$. These sigma points are used as input of a function g, which is an approximation of the state transition probability function. This is used to generate $\bar{\mu}_t$ and $\bar{\Sigma}_t$, the transformed Gaussian distribution. The same procedure is then used to produce $\bar{Z}_t$, the vector of likelihoods of observations given the calculated sigma points.

Figure 5:
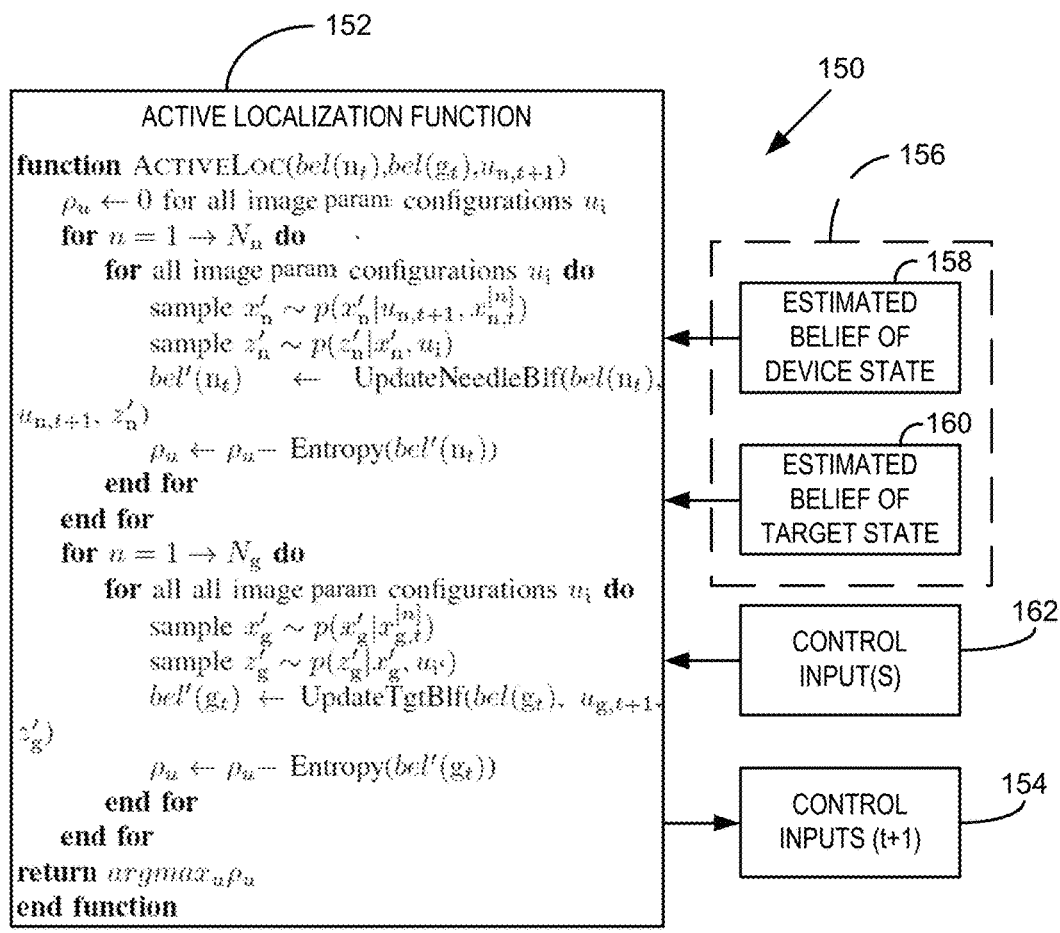
FIG. 5 depicts an example of an active localization function for generating control parameters for active localization.

FIG. 5 depicts an example of an active localization method 150 (e.g., corresponding to active localization method 36 of FIG. 1). The active localization method 150 can include an active localization function 152 programmed to generate corresponding system control inputs 154 for a next time step. The active localization function 152 can generate the control inputs 154 based on an estimated belief of system state (e.g., bel(x)) 156, which can include a corresponding estimate belief of device state 158 and a corresponding estimated belief of target state 160. For example, the estimated belief of device state 160 can be provided by any of the belief state estimators (e.g., estimator 52, function 80, function 100, function 120) as disclosed herein.

The active localization function 152 determines the control inputs 154 based on the estimated belief of system states 156 over a range of corresponding control inputs. As disclosed herein, in some examples, device control inputs can be separately determined by a corresponding instrument motion planner and controller based upon the current state beliefs 158 and 160 that have been estimated for the current time stamp t. In other examples, the active localization function can implement active control for the instrument system in a manner similarly to the active control for the imaging system disclosed herein.

By way example, the active localization function block 152 contains an example of pseudo code for executable instructions that the active localization function can be programmed to implement for providing active control inputs 154. In the example of FIG. 5, the active localization of performs a greedy algorithm based on entropy minimization. In the algorithm, the entropy of the needle's and target's beliefs, which may be implemented using particle filters or unscented Kalman filters, are estimated using the differential entropy calculation. Here it is assumed that the device control input $u_n$ is separately determined by a needle motion planner and controller based on the current beliefs of the system state (e.g., device and target states). However, in other examples, the active control implemented by the function 152 can actively determine both device and target control inputs. The dependence of the needle and target measurements to the configuration of the image parameters, specified by $u_t$, is explicitly included in the measurement model expression (e.g., as disclosed with respect to models 40 and 46 of FIG. 1).

At each time step (t), the active localization function 152 determines samples of estimated device state and samples of expected image outputs over a range of possible image parameters $u_i$ (e.g., defined by sample generator 56). The hypothetical estimates are employed to determine an expected (e.g., future) device belief state bel' ($n_t$), which belief state updated by the Bayes filter function based on current device belief state device bel($n_t$), device control inputs $u_{n,t+1}$ and hypothetical measurements $z'_n$. The function 152 then computes the expected information gain ($\rho_u$) for each of the possible image parameters u to determine the set of image parameters that is most likely to maximize the information gain about the current state. In this example, the active localization function 152 calculates the information gain (IG) as the expected change in the entropy of the device belief state. The expected change in the entropy of the device belief state is calculated as difference between the entropy of the current device belief state and the expected device belief state bel'($n_t$) resulting from the set of potential measurement values for the corresponding image parameters. For ease of explanation, it is to be understood that the entropy of the current device belief state is omitted in the equation for $\rho_u$ as it has the same value for all of the different possible image parameters considered. The active localization function 152 can perform the same process with respect to the target state beliefs to minimize the associated entropy for use in determining the set of control inputs to maximize information gain for the next time step.

Figure 6:
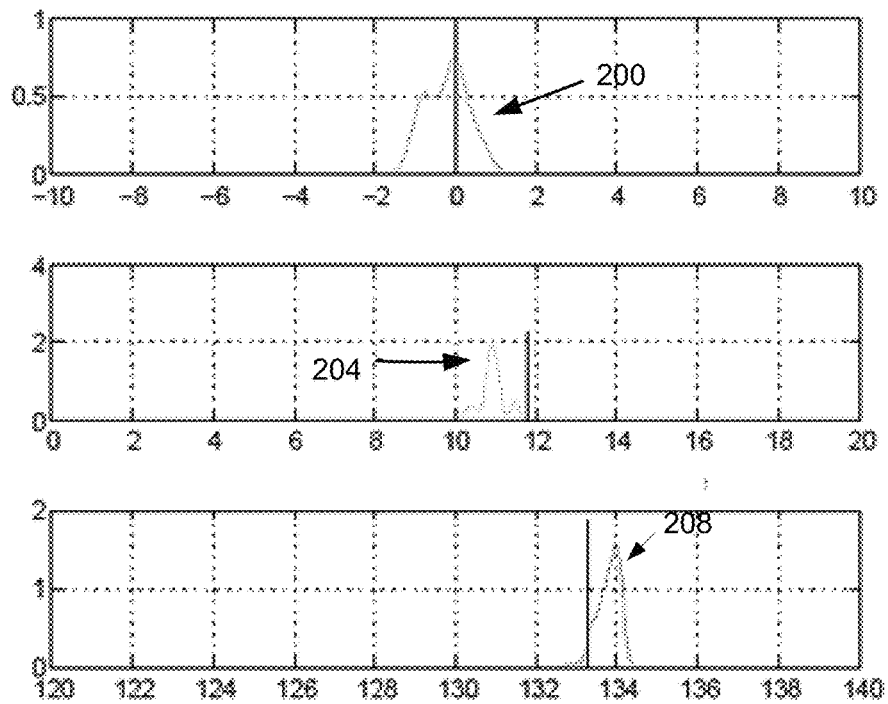
FIG. 6 depicts graphs of example belief probability density function estimates for an instrument location, which can be determined by the function of FIG. 3.
Figure 7:
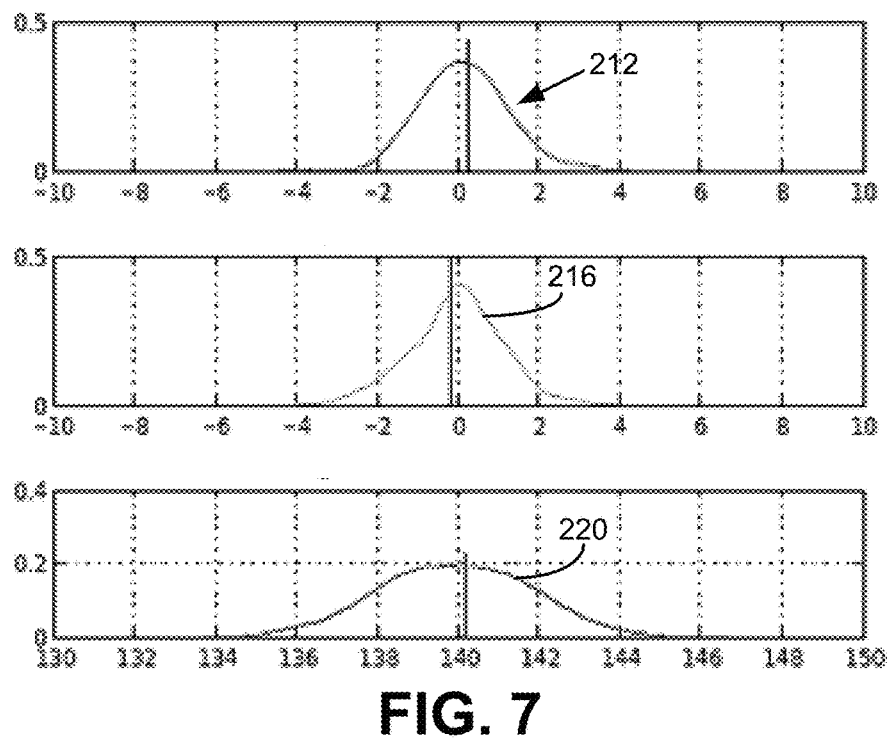
FIG. 7 depicts graphs of example belief probability density function estimates for target location, which can be determined by the function of FIG. 3.

FIG. 6 depicts examples of device tip location belief probability density functions for each of the corresponding x, y and z coordinates demonstrated at 200, 204 and 208. The solid lines in each of the coordinate plots of FIG. 6 indicate the actual location by way of comparison. In the example of FIG. 7, target belief probability density functions are demonstrated for each of the x, y, and z coordinates, demonstrated at 212, 216 and 220, respectively. Corresponding known target coordinate locations are demonstrated by solid lines in FIG. 7.

Figure 8:
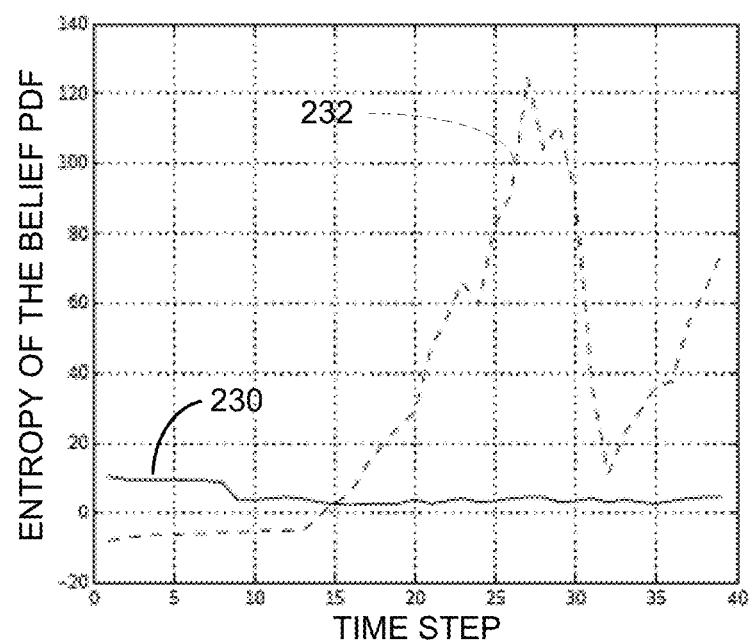
FIG. 8 is a graph of entropy calculated over a plurality of time steps based on the PDF estimates of FIGS. 6 and 7.
Figure 9:
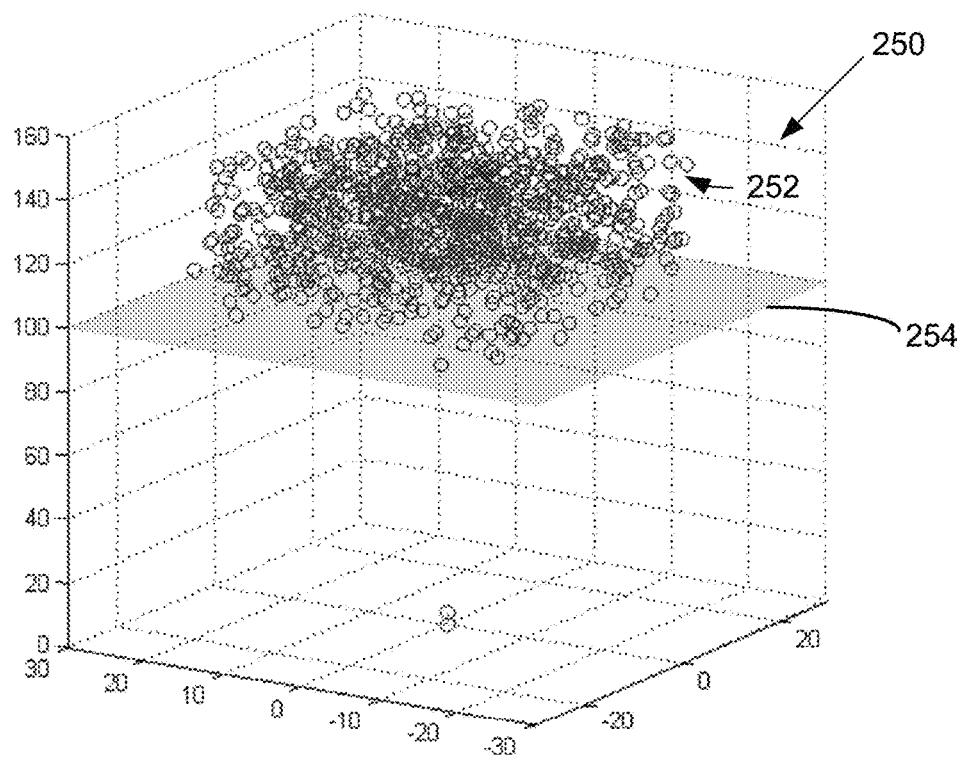
FIG. 9 depicts an initial particle distribution for location of an unknown target in an image space based on location estimates determined according to a particle filter function.

FIG. 8 depicts an example of the change of entropies over a plurality of time steps that can be determined by an active localization function (e.g., function 36 or 152 disclosed herein). In the example of FIG. 8, change in entropies for the device tip locations are demonstrated by dashed lines 232. The change of entropies over time for the target location beliefs are demonstrated at 230. From FIG. 8 it is demonstrated that the active localization method can successfully alternate between imaging the target and the device to minimize the total entropy of the corresponding aggregate belief.

Figure 10:
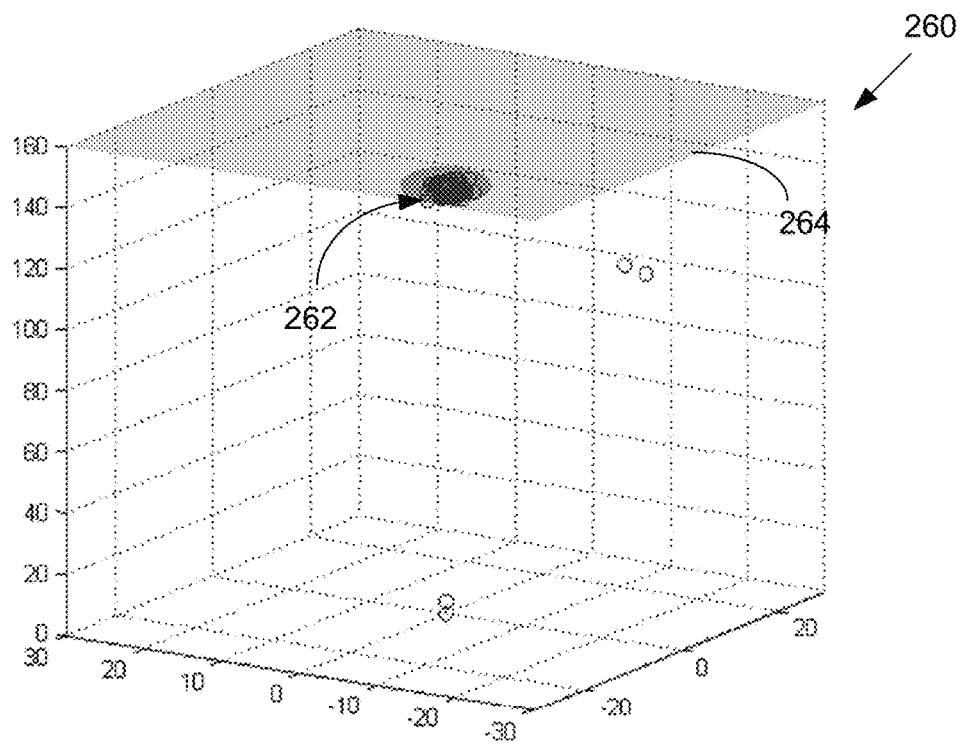
FIG. 10 depicts an example of a target being localized in an image space using a particle filter function.

FIGS. 9, 10, 11, and 12 demonstrate examples of particle filtering tracking of a device tip and target that can be tracked in three dimensional space (e.g., determined by particle filter function 100 of FIG. 3) as the device is inserted in media toward a target site (e.g., in patient tissue). The graph 250 of FIG. 9 demonstrates an initial particle distribution 252 when the location of the target is unknown shown relative to an associated image plane 254. FIG. 10 demonstrates a three-dimensional plot 260 after a corresponding target has been localized at 262 such as at an end of a linear scanning phase implemented by the imaging system (imaging system 12) for an imaging plane 264.

Figure 11:
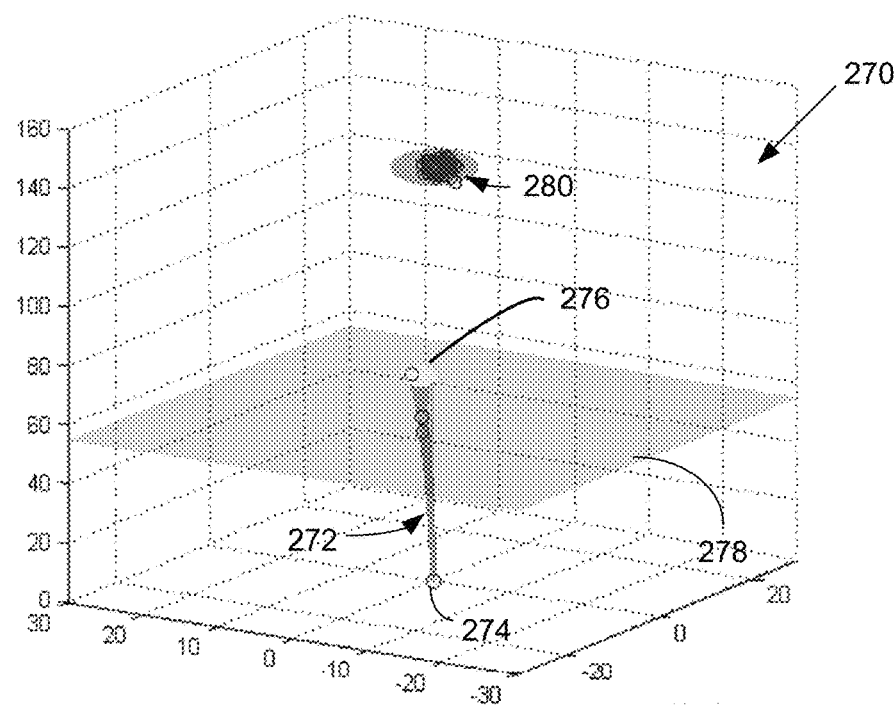
FIG. 11 depicts an example of particle distribution for location of a target in an image space during an instrument insertion procedure where the instrument and target are localized according to a particle filter function.

FIG. 11 depicts an example of a plot 270 of particle distributions that can be computed by a particle filter function (e.g., particle filter function 100 of FIG. 3) to estimate locations of the target and device. Particles for tracking trajectory of an instrument are demonstrated at 272. The trajectory 272 extends between an insertion point 274 and an intermediate location 276, such as the current belief estimate for the location of the distal end of the instrument that lies in an image plane that has been actively localized as disclosed herein. The trajectory 272 can be determined over time as the instrument is advanced toward a target 280.

Figure 12:
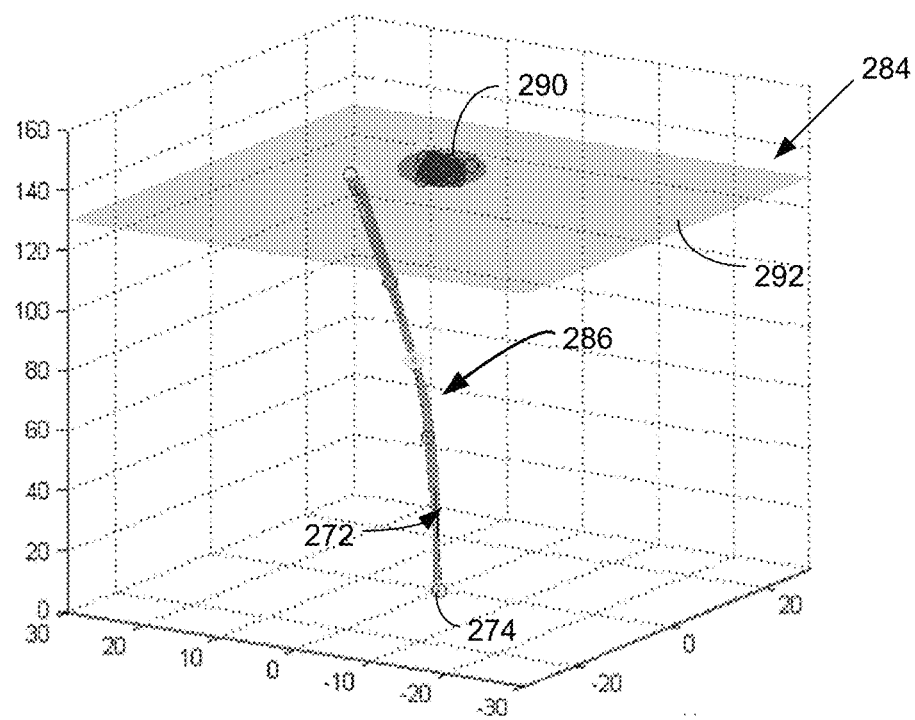
FIG. 12 depicts an example of particle distribution for location of a target and instrument at the end of the procedure of based on location estimates determined according to a particle filter function.

FIG. 12 depicts an example of a plot 284 of particle distributions that can be computed by a particle filter function (e.g., particle filter function 100 of FIG. 3) to provide particle distributions to estimate location of the target and device at the end of the procedure. In FIG. 12, the trajectory extends between the insertion point 274 and end location 288 that resides in plane 292, where the target location 290 has been estimated to reside.

FIG. 13 depicts a plot of an instrument (e.g., a needle or catheter) 300 demonstrating an example instrument configuration being inserted into simulated tissue. The instrument 300 includes four control points 302, 304, 306 and 308 according to an instrument model. In the example of FIG. 13, the path between control points for the instrument demonstrates flexion along its length, which is due to motion model accounting for flexible needle insertion into a relatively stiffer media (e.g., tissue). FIG. 14 depicts plots of a plurality of samples of instrument configuration 310 from a posterior distribution of instrument shape according to execution of the instrument motion model of FIG. 13.

Figure 15:
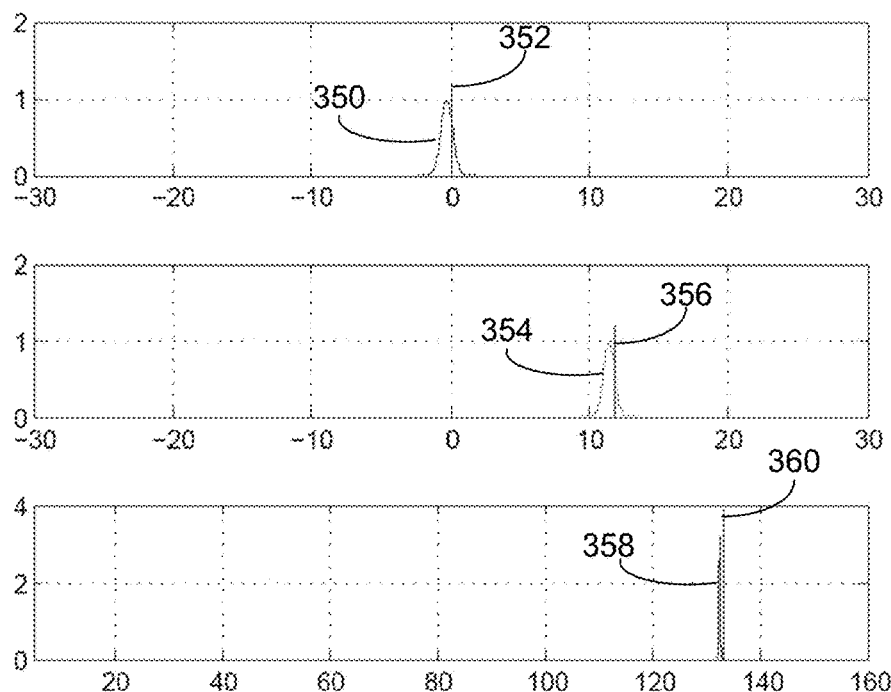
FIG. 15 depicts graphs of example belief probability density function estimates for instrument location, which can be determined by a Kalman filter function.

FIG. 15 depicts graphs 352, 354 and 358 of example probability density functions for instrument location in each of respective x, y and z coordinates of three dimensional image space. The probability density functions 352, 354 and 358 demonstrate estimates that can be determined by an unscented Kalman filter function (e.g., function 120 of FIG. 4). Thus, the estimates have smoothed Gaussian distribution. Solid lines in the graphs demonstrate actual known needle tip locations for comparative purposes.

Figure 16:
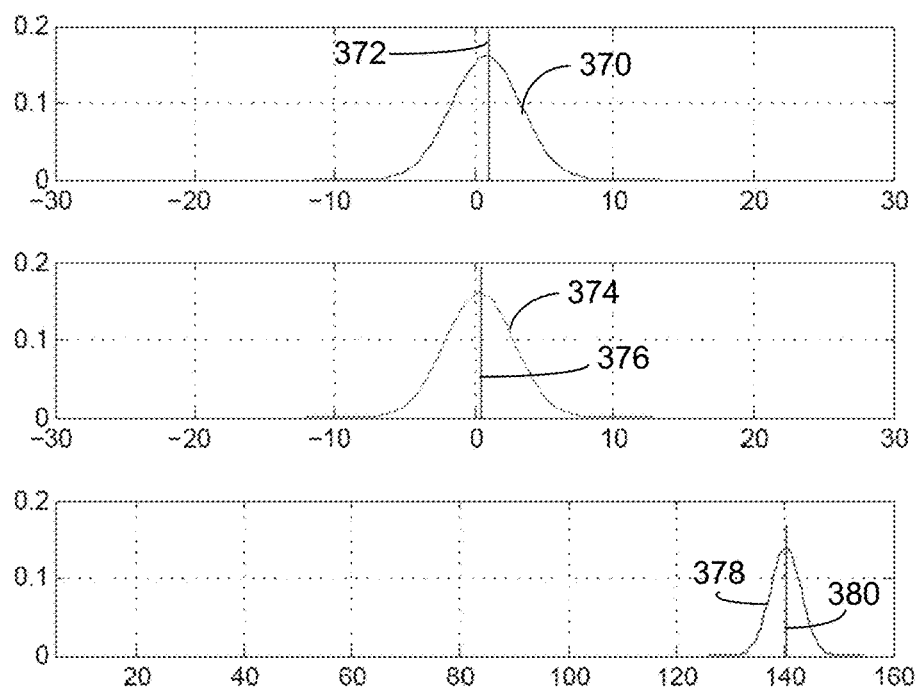
FIG. 16 depicts graphs of example belief probability density function estimates for target location, which can be determined by a Kalman filter function.

FIG. 16 depicts graphs 370, 374 and 376 of example belief probability density function estimates for target location for respective x, y and z coordinates. Similar to the example of FIG. 15, the probability density functions 370, 374 and 376 demonstrate target estimates that can be determined by an unscented Kalman filter function (e.g., by function 120 of FIG. 4).

Figure 17:
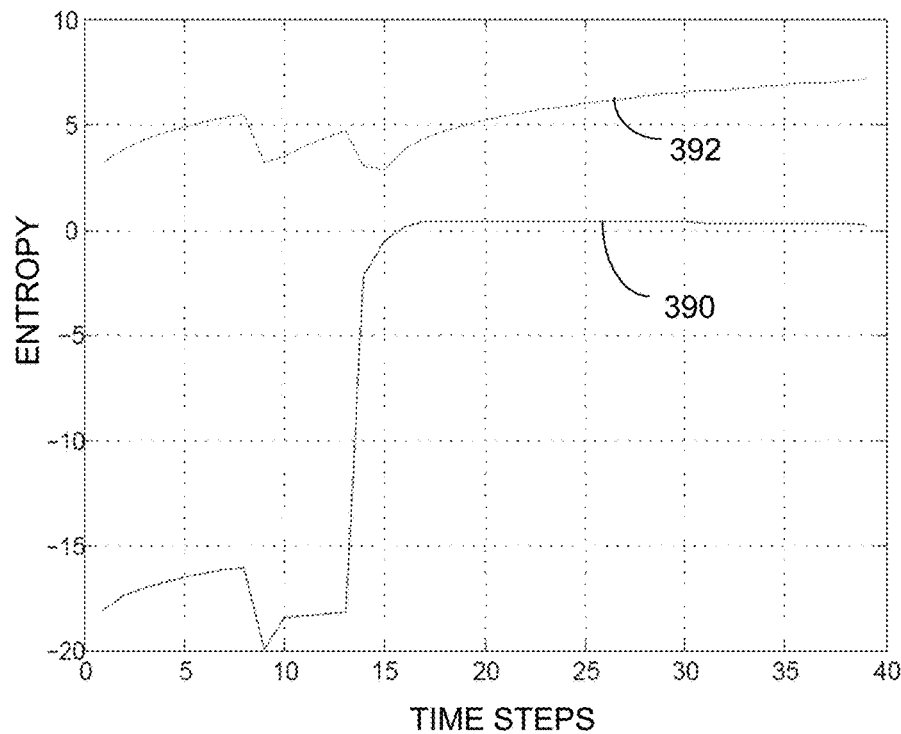
FIG. 17 is a graph illustrating entropy changes calculated over a plurality of time steps based on the PDF estimates of FIGS. 15 and 16.

FIG. 17 is a graph of depicting a change in entropy calculated over a plurality of time steps based on the PDF estimates of FIGS. 15 and 16. For example, entropy for the instrument belief location estimates is demonstrated at 390 and entropy for the target belief location estimates is demonstrated at 390. As with the particle filter function, the Kalman filter function successfully alternates between imaging the target and the needle in order to minimize the total entropy of the belief.

Figure 18:
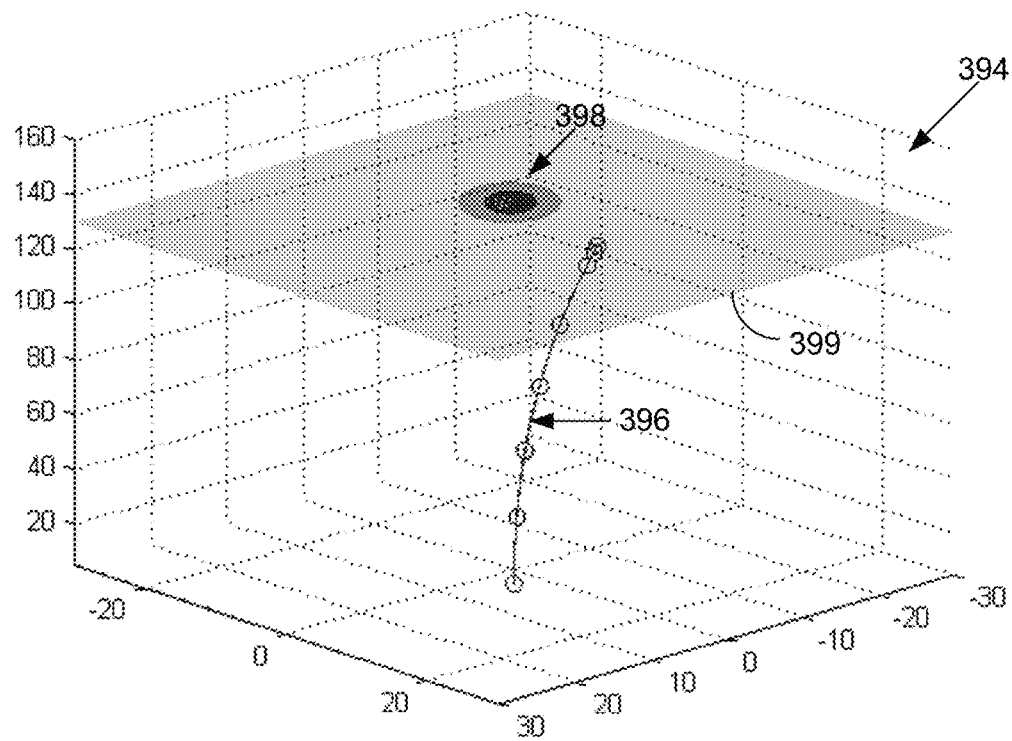
FIG. 18 depicts an example of location of a target and instrument based on location estimates determined according to an unscented Kalman filter function.

FIG. 18 depicts an example plot 394 of estimated location of a target and instrument based on location estimates determined according to an unscented Kalman filter function (e.g., UKF function 120 demonstrated in FIG. 4). The plot 394 illustrates a trajectory path 396 estimated over a sequence of time steps between an insertion point and a target 398. In the example of FIG. 18, a center of the target resides in a corresponding image plane 399 that has been actively localized based on UKF function, as disclosed herein.

Figure 19:
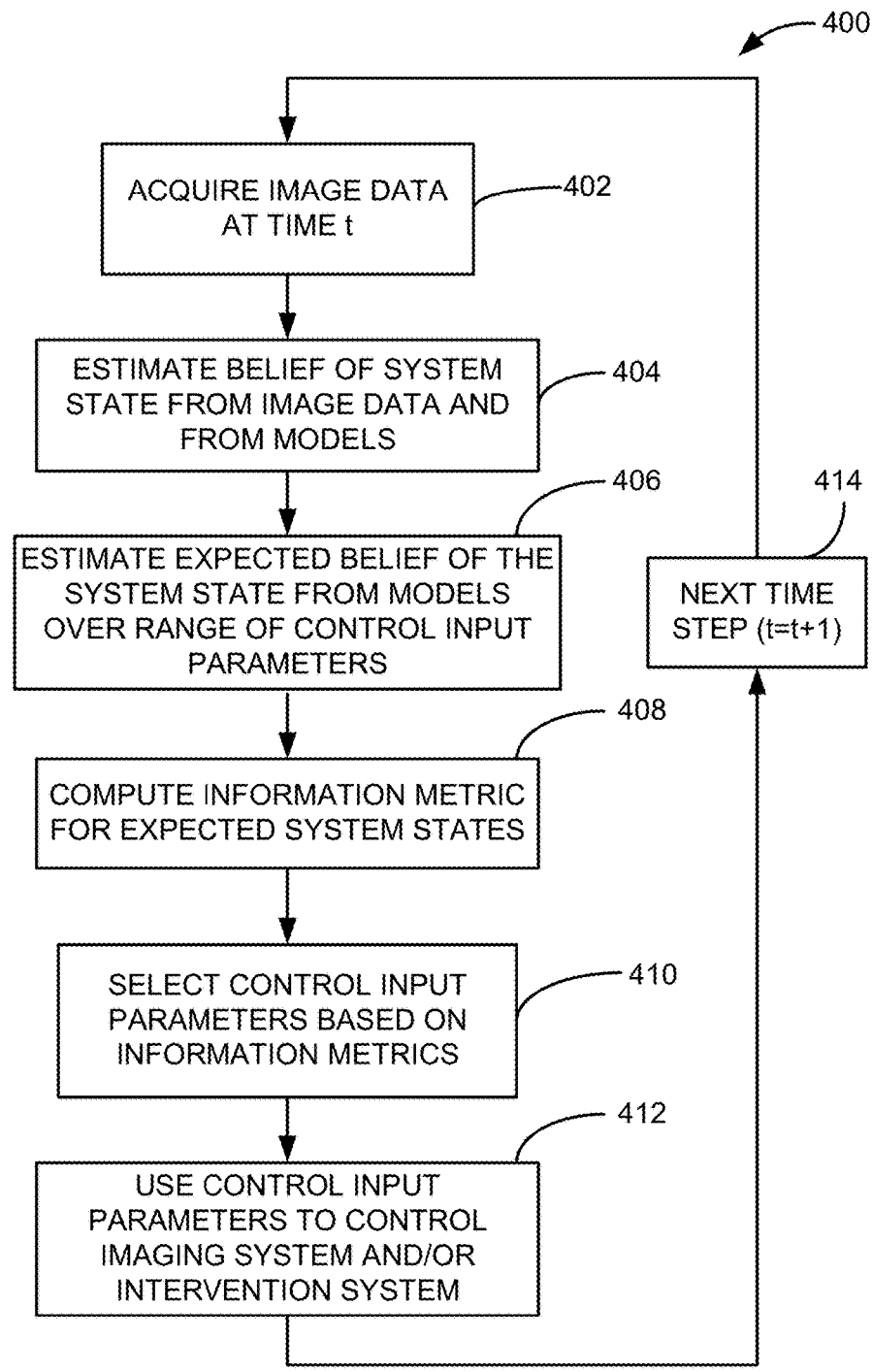
FIG. 19 is a flow diagram depicting an example of a method for active localization.

In view of the foregoing structural and functional features described above, an example method will be better appreciated with reference to FIG. 19. While, for purposes of simplicity of explanation, the example method of FIG. 19 is shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method. The example method of FIG. 19 can be implemented as instructions and data stored in one or more machine readable media (e.g., program code). The stored instructions can be executed by a processor to perform the method in relation to the data that is stored in memory accessible by the processor.

FIG. 19 depicts an example of a method 400 that can be utilized to perform active control based on intra-operative medical imaging. The active control can be used to control one or more imaging systems (e.g., imaging system 12) and/or an intervention system (e.g., intervention system 14). As disclosed herein, the method 400 can be used intra-operatively such as during a procedure in which a corresponding device (e.g., an ablation catheter or other object), is advanced in a patient's body into contact with a target anatomical site. As mentioned the target site can be fixed (e.g., be stationary) within a corresponding three-dimensional coordinate system or the target or a portion thereof may be movable (e.g., part of a patient's anatomy such as the lungs, heart, a valve or the like). The method 400 is an iterative method that can be repeated for each of a plurality of time steps, where each time step corresponds to an image acquisition phase.

At 402, image data (e.g., image data 34) is acquired from the image system (e.g., image system 12) for a given time step. The image data represents an image space in which an instrument and/or a target that includes a patient's anatomy (e.g., image space 16). Each of the imaging system and the intervention system can operate according to respective control input parameters. The input parameters can be set in response to a user input as well as based on sensed conditions associated with their operations. The control input parameters can also be provided using active control via a control interface as disclosed herein.

At 404, a given belief of system state for the given time step is estimated. The given system state for the given time step includes an estimate of instrument state and target state that are determined from corresponding measurement and motion models (e.g., measurement model 46 and motion model 40). As disclosed herein, each of the measurement and motion models are computed based on previous state information, the acquired image data and control input parameters for each respective time step.

At 406, an expected belief of system state is estimated from the models (e.g., models 40 and 46) based on the given belief of system state for the current time and over a range of control input parameters from one or both of the imaging system and the intervention system. The expected belief of system state can be estimated, for example, by a Bayesian filter function (e.g., function 80), such as can be implemented as a particle filter function (e.g., function 100) or an unscented Kalman filter function (e.g., function 122). It is understood that other filter functions could be utilized to estimate each of the given belief of system state for the current time stamp or the expected belief of system state such as disclosed herein. In some examples, the estimating at 404 and 406 can be implemented based on a priori information such as by seeding the respective filter function based on known location for one or more previous time steps. In other examples, the initial belief estimates can be unseeded and derived based upon an initial set of information (e.g., random or predetermined information) that is provided.

At 408, an information metric is computed (e.g., by information metric calculator 54) for each of the expected beliefs of the system states (estimated at 406). For example, the information metric can be computed by determining an entropy for each of the estimated expected beliefs of system state. In some examples, the estimated beliefs of system state and associated information metrics can be determined separately for different components in the system, such as for device state and for target state, as disclosed herein.

At 410, control input parameters are selected (e.g., by control input selector 58) based on the information metrics computed at 408. As disclosed herein, the selection at 410 can be implemented by a greedy algorithm based on the control inputs determined to maximize information gain from the current state information. As mentioned, the maximum information gain can be implemented based on entropy minimization.

At 412, the selected control input parameters can be used to control the imaging system and/or the intervention system. For example, the control input parameters can set imaging parameters such as including image plane, image spatial resolution, image temporal resolution, scan ray image area, and the like. Control inputs for the intervention system will vary depending upon the type of intervention that is implemented by the system. For the example of using electrical therapy delivery for the intervention system, control input parameters can include amplitude, frequency, duration or duty cycle and the like. For the example of an intervention system associated with robotic actuation of a device, control input parameters can include an identification of a location in a given coordinate system, a velocity (e.g., including a trajectory direction and speed). Controls of the intervention system can interpret the control inputs generated by the method 400 for each time step and/or in response to user inputs to dynamically adjust outputs provided by the intervention system for each time step that the control inputs are provided during the method 400. Additionally, the control inputs can be combined with other data and feedback (e.g., location and/or tissue condition information from the imaging system) as part of implementing active catheter control.

As a further example, FIG. 20 depicts an example of an intervention system 500 corresponding to delivery of ablation therapy via a catheter 502 that is insertable percutaneously into a patient's body, demonstrated schematically at 504. This system 500 includes an intervention control system 506 that is configured to implement one or more interventional control functions to operate one or more devices for diagnosing and/or treating the patient's body 504. The system 500 also includes an imaging system demonstrated in this example as a magnetic resonance imaging system 508; although, other imaging modalities can be used as disclosed herein.

The system also includes an active control method 510 to provide control inputs to the imaging system 508 and the invention control system 506. The active control method can be implemented separately from or as part of one or both of the imaging system 508 or intervention control system 506. The active control method 510 can be implemented as machine instructions (executable by one or more processors) to generate one or more control inputs in response to imaging data acquired by the imaging system 508. The active control method can implement active localization and control (e.g., method 36 or 152) for the imaging system 508 and the intervention control system 506.

The imaging system 508 can acquire image data of the patient's body including the catheter 502 and the corresponding target site 512. For example, the MRI system 12 can image the location of the catheter tip (of device 18) and the target tissue 20 on the pulmonary vein or other tissue structure and provide corresponding image data in substantially real-time (e.g., generate a new set of image data about every 20 ms to 50 ms). The image data can be preprocessed by the imaging system 508 and utilized by the active control method 510 to provide corresponding input control parameters to the MRI system 508 for active sensing of the target 512 and catheter device 502. Additionally, the active control method 510 can provide corresponding input control parameters to the intervention control system 506 for controlling intervention with respect to the patient's body 504. The imaging system 508 can further generate an output visualization to provide a real-time display 509 according to the image being acquired.

In the following example, the intervention is provided via the catheter 502 that is inserted percutaneously. However, it is understood that the intervention system 500 can implement in variety of other diagnostic and treatment devices, which may be inserted internally within the body 504 or be provided externally (e.g., sources of radiation) applied to the internal target 512 that is actively localized.

In the example of FIG. 20, the intervention control system 506 includes a robotic motion control 516 to control operation of an arrangement of motion components (e.g., motors, actuators, coils or the like) to position the catheter 502 at a desired position relative to the patient's body. For example, the robotic motion control 516 can include a motion planning module 518 to determine control parameters 520 for adjusting the position and/or orientation of the catheter 502 in a coordinate system of the patient and imaging system 508. For example, the motion planning module 518 and robotic motion control can be programmed to actively control motion of the catheter and to compensate trajectory for performing ablation according to the planning methods and controls disclosed in *Task-Space Motion Planning of MRI-Actuated Catheters for Catheter Ablation of Atrial Fibrillation*, Greigarn, T. et al., IEEE RSJ International Conference on Intelligent Robots and Systems (September 2014), which is incorporated herein by reference. The robotic motion control 516 can be fully automated in response to the control parameters 520 provided by motion planning 518 and the active control method 510. In other examples, the robotic motion control can be co-robotically controlled, meaning that the parameters 520 can be modified based on user interaction and resulting catheter positioning is robotically assisted.

In the example of FIG. 20, the system 500 includes an axial actuation component 514 that can be utilized to adjust the axial position of a distal end of the catheter 502 in response to the control signals provided by robotic motion control 516. For example, the motion planning module 518 can determine control parameters 520 for axially adjusting the position and/or orientation of the catheter 502 in a coordinate system of the patient and imaging system 508. The axial actuation 514 can include a linear actuator (e.g., linear motor or servo motor) configured to advance the catheter body generally in an axial direction along a trajectory to position the catheter tip 522 into contact with the target 512.

In addition to adjusting the position of the catheter axially along the path via the actuation 514, the intervention control system 506 can include catheter steering control 524 to provide for translational motion with respect to three orthogonal axes in three-dimensional space. For example, the catheter steering control 524 controls current applied to coils attached to the catheter body to affect deflection of the catheter in two orthogonal axes relative to its longitudinal axis. For example, the catheter body can include a polymer tubing that is embedded with multiple sets of corresponding current carrying coils.

The catheter 502 can be steered in a couple of different manners. First of all, the magnetic field of the MRI system 508 can be used to directly actuate the catheter. Alternatively or additionally, a small robot (e.g., placed near the patient's knees) can move the catheter 502 axially, rotate, and bend. The catheter itself would have coils embedded to help identify its location and orientation from the image data.

As a further example, the catheter can be implemented as a MRI-actuated steerable catheter (see, e.g., FIG. 21) that can cause deflection along the catheter body along transverse to the longitudinal axis thereof in response to current supplied by the robotic motion control 516. For example, current through the coils generates magnetic torque when subjected to the magnetic field provided by the MRI system 508. The currents can be controlled remotely via the catheter steering control 524 automatically or in response to a user input to steer the catheter in conjunction with the axial actuation 514 to move the distal end 522 of the catheter along a given trajectory, such as to contact the target site. The catheter motion can be achieved by interlacing of the imaging and catheter control signals in the MRI system.

As the moment applied by the actuation 514 is dependent on the relative orientation of the actuator coils and the magnetic field vector of the MRI system 508, the external loading on the catheter changes with deflection. Therefore, the robotic motion control 516 is configured to calculate forward kinematics (catheter deflection for a given set of actuator currents) requires the solution of a system of nonlinear equations. The robotic motion control 516 also computes corresponding inverse kinematics because of the complexity of the kinematics. In the given formulation, it would be possible to derive analytic expressions for the Jacobian. That is, Jacobian-based methods can be effectively used for inverse kinematics calculations. For example, the robotic motion control 516 of intervention system 506 can employ the damped least squares method, which avoids stability problems in the neighborhoods of singularities.

As a further example, in addition to the target trajectory, robotic motion control 516 can employ generalized adaptive filters to estimate the uncertainty of the motion (in the form of estimation error covariance). The estimated trajectory will then be used as a feed-forward control signal in a stochastic receding horizon model predictive controller. Combining the estimated upcoming trajectory of the target tissue (including estimation error covariances) and the probabilistic model of the catheter dynamics (including the "random perturbations" from non-steady blood flow), the motion control can solve an optimal control problem minimizing the tracking error covariance over the control horizon using differential dynamic programming. As one example, the catheter system can be modeled as disclosed in *Three Dimensional Modeling of an MRI Actuated Steerable Catheter System*, Liu, T. et al., IEEE International Conference on Robotics and Automation, May 2014, which is incorporated herein by reference.

As disclosed herein, the location of the catheter tip 522 and the target tissue 512 are simultaneously measured by the intra-operative MRI system 508 in real-time to implement the active localization and control disclosed herein. For instance, the active control method 510 can implement an active sensing scheme to control the intra-operative imaging system 508, optimally selecting position and orientation of the image slices to be acquired as well as other imaging parameters, for optimal localization of the target and the catheter. The motion planning 518 and steering 524 of the robotic motion control 516 utilize the target and catheter location information extracted from the images acquired by the intra-operative MRI system as well as active control inputs selected for each time step to actively control the catheter tip to track the target tissue.

Once the distal end of the catheter 522, which includes an ablation delivery structure (e.g., one or more electrodes), is in contact with the target site 512, the ablation control 528 can deliver ablated therapy to the target. The ablation control 528 can operate based upon a set of ablation parameters 530 and an activation function 532 to supply the ablative therapy via the delivery mechanism (e.g., at the distal end 522) according to the parameters 530. For example, the ablation control 528 can supply RF energy to the electrode at the distal end 522 of the catheter 502 and activate the RF energy to ablate the tissue at the contact site of the target 512 in response to the parameters 530 specifying amplitude, frequency, duration (e.g., duty cycle) of energy. During application of the therapy, the intervention control system 506, including robotic motion control 516 and catheter control 522, further can adjust the position of the distal end of the catheter across the target 512 to achieve a sufficient amount of ablation on the target site. For example, the distal end of the catheter can be moved in a sequence of patterns and ablate the tissue at each of a plurality of locations across the surface of the target tissue. The sequence of patterns can be automated or responsive to user controls.

In order to achieve successful ablation, the catheter tip 522 needs to remain in constant contact with the tissue when the activation component 532 applies ablative therapy. Such contact should be maintained and follow the trajectory specified by the operator, despite disturbances from blood flow and tissue motions, as mentioned above. Accordingly, in some examples, the robotic motion control 516 dynamically corrects the position of the catheter to compensate for (e.g., cancel) the cardiac motions and/or perturbations resulting from blood flow. For instance, the robotic motion control 516 can employ active relative motion cancellation methods. The motion control 516 actively tracks the motion of the deformable tissue, so as to dynamically adjust the position of the tip of the catheter to remain stationary relative to the tissue. Once the tip of the catheter is "stationary," the motion planning can be performed with respect to a stationary tissue frame, and the resulting catheter motion can be added to the active tracking motion.

To reduce the computational complexity associated with such active tracking, the motion control take advantage of the quasi-periodic nature of the target tissue motion (e.g., wall motion synchronized with the patient's heart beat), and the perturbations on the catheter motion due to non-steady blood flow. The motion control thus can employ generalized adaptive filters for estimating the upcoming motion of the target tissue and the catheter. Once estimates of the upcoming catheter and target tissue motions are available, even if they are not perfect, these estimate can be used to reduce the uncertainties in system dynamics. Reduced uncertainty facilitates the use of unimodal distributions in representing uncertainties in the models being implemented and can even enable use of linearized models in some examples.

During an example RF ablation procedure, the robotic motion control 516 automatically steers the catheter while energy is applied to the catheter 502 and the target cardiac tissue is burned. As mentioned, the robotic motion control 516 employs active relative motion cancellation algorithms so that the catheter moves with the heart to assure that there is constant contact throughout the ablation. The catheter automatically traces the "burn path" as defined by the operating physician, such as can be determined from a prior EP study. Throughout this time, the MRI tracks heat generation in the wall of the heart to guard against full thickness burns. In some examples, the EP study can be performed using the same catheter 502 that is used for ablation, such as by sensing electrical potential via one or more electrodes attached at or near the distal end 522. In other examples, another different sensing catheter can be utilized, which may be controlled actively based on imaging data, as disclosed herein.

As described above, the system 500 synergistically integrates high speed magnetic resonance imaging and robotic motion control technologies. For example, the robotic motion control 516 can control the catheter position to automatically (or semi-automatically) trace a "burn path", as defined by the operating physician (e.g., determined from a prior electrophysiology (EP) study). Throughout this time, the MRI system 508 can track heat generation in the wall of the heart to guard against full thickness burns, and deactivate the ablative therapy if sufficient heat penetrates too deeply into the target cardiac tissue. In some examples, the EP study can be performed using the same catheter 502 that is used for ablation. In other examples, another different sensing catheter can be utilized, which may be controlled actively based on imaging data, as disclosed herein.

The system 500 has several advantages over other techniques and technologies for cardiac ablation therapy, as it would allow a more tailored treatment to be performed. For example, intra-operative real-time availability of MRI, with its superior tissue discrimination capabilities, would allow immediate evaluation of the substrate depth and lesion created by ablation. Remote steering and high accuracy catheter tip position control, with active motion compensation, would allow for precise ablation. The operator would have improved situational awareness, as the intra-operative information, including the electro physiological map, catheter trajectories, and tissue measurements obtained from real-time magnetic resonance imaging, is mapped back and displayed to the operating physician on the 3D static reference visualization of the cardiac anatomy. Moreover, the patient will not be exposed to ionizing radiation during the procedure, as fluoroscopy will not be used.

As a further example, FIG. 21 depicts an enlarged view of the catheter 502 which includes a plurality of coil sets 542, 544, and 546. The catheter steering control (e.g., corresponding to control 522) is electrically connected with each of the coil sets for supplying electrical currents through one or more of the coils at each coil set to effect deflection of the catheter in a desired way in response to the magnetic field generated by the corresponding MRI system (6508). In the example of FIG. 21, each of the coil sets 542, 544, and 546 includes three orthogonal coils. In the cross-sectional view of FIG. 21A, the coil set 542 is shown to include one coil 552 wound circumferentially around or embedded in the catheter body. Another coil 554 includes coil windings disposed on diametrically opposed sides of the catheter body, such as in juxtaposition with respect to the coils 552. Another coil 556 can be disposed on diametrically opposed sides of the catheter body in juxtaposition with respect to the coils 552 and extending orthogonally with respect to the coils 554. Each of the coils 552, 554 and 556 has a number of turns wound around an axis, in which each of the respective axes is orthogonal to each other. In the particular orientation shown of FIG. 21A, the coil 554 includes windings around an axis that extends vertically through catheter body, and the coil 556 includes windings around another axis that extends horizontally through catheter body. Thus, the respective currents can be selectively applied to each coil to achieve desired steering of the catheter 502 in response to the magnetic field provided by the associated MRI system 508. The use of multiple coils in the catheter 502 also mitigates actuation singularities that can occur in other designs. The multiple coil sets further enable controlled deflections of the catheter tips in three-dimensional space.

As a further example, to facilitate positioning the catheter tip via MRI actuated deflections (e.g., by energizing respective coils), the catheter body can be constructed from a material having a Young's modulus that is less than about 200 MPa (e.g., about 100 MPa or less). Examples of some materials include polyurethane, latex rubber and silicone rubber, each of which has a Young's modulus that is less than about 100 MPa, and in some cases a Young's modulus less than about 50 MPa to afford increased deflection performance.

Although the initial focus of the disclosed technology is atrial fibrillation cardiac ablation therapy, other catheter based cardiac procedures would be amenable to a similar approach. For example, percutaneous valves could be placed using a catheter which would automatically account for motion. Furthermore, there has been a great deal of work to expand the use of external beam radiation techniques to multiple different areas of the body. This general approach could be used to automatically guide the external beam for ablation purposes.

In view of the foregoing structural and functional description, those skilled in the art will appreciate that portions of the invention may be embodied as a method, data processing system, or computer program product. Accordingly, these portions of the invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer (e.g., as part of the imaging system), or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:
   acquiring image data from an imaging system for a given time step, the image data representing at least one of an instrument and a target within an image space that includes patient anatomy, the imaging system and an intervention system operating according to control input parameters;
   estimating a given belief of system state for the given time step, the given belief of system state for the given time step including an estimate of instrument state and target state determined from corresponding measurement and motion models computed based on the acquired image data and the control input parameters for the given time step, wherein the estimating the given belief of system state comprises using a Bayes filter function to compute the given belief of system state, the Bayes filter function comprises at least one of a particle filter to estimate a posterior density representing the given belief of system state or a Kalman filter function to estimate a mean and a covariance matrix representing the given belief of system state;
   estimating an expected belief of system state for a subsequent time step based on the estimated given belief of system state and based on the corresponding measurement and the motion models computed over a plurality of different control inputs parameters for at least one of the imaging system and the intervention system;
   computing information metrics for each of the expected belief of system states estimated for the subsequent time step; and
   selecting the control input parameters to control the at least one of the imaging system and the intervention system for the subsequent time step based on the computed information metrics.

2. The method of claim 1, further comprising:
   controlling the at least one of the imaging system and the intervention system the for the subsequent time step; and
   repeating each of the acquiring estimating, computing, selecting and controlling over a plurality of next time steps.

3. The method of claim 1, wherein computing the information metric comprises computing an entropy of the estimated expected belief of system states, the selected control input parameters being selected to minimize the entropy.

4. The method of claim 1, wherein the control input parameters for the imaging system include at least two of a position of an imaging plane in the image space, an orientation of the imaging plane in the image space, a resolution, a scan speed, a scan duration and a scan area within the image space.

5. The method of claim 1, wherein the imaging system comprises an intraoperative imaging modality that operates based on imaging control input parameters, at least some of the imaging control input parameters being selected part of the control input parameters based on analysis of the computed information metrics.

6. The method of claim 5, wherein the intraoperative imaging modality comprises one of magnetic resonance imaging, ultrasound imaging, radiography, thermography or tomography.

7. The method of claim 1, wherein estimating the expected belief of system state further comprises using the Bayes filter function to compute the expected belief of system state.

8. The method of claim 1, further comprising controlling each of the imaging system and the intervention system the over time based on the control input parameters.

9. The method of claim 8, wherein control of the intervention system employs Jacobian-based controls or inverse kinematics based methods to control at least one parameter of the instrument.

10. The method of claim 1, wherein the instrument comprises a catheter and the intervention system includes a catheter control system for actively controlling the catheter, the method further comprises adjusting a position of the catheter relative to an estimated location of the target based on the control input parameters.

11. The method of claim 10, wherein the catheter comprises a plurality of multi-axial coils disposed about the catheter, the method further comprising positioning the catheter relative to the target in response to selectively applying current to the coils and in response to a magnetic field provided by the imaging system.

12. The method of claim 11, further comprising applying therapy from the catheter to the target.

13. A method comprising:
    acquiring image data from an imaging system for a given time step, the image data representing at least one of an instrument and a target within an image space that includes patient anatomy, the imaging system and an intervention system operating according to control input parameters;
    estimating a given belief of system state for the given time step, the given belief of system state for the given time step including an estimate of instrument state and target state determined from corresponding measurement and motion models computed based on the acquired image data and the control input parameters for the given time step,
    wherein the corresponding measurement model comprises:
    an instrument measurement model to compute a probability density function for the instrument to represent uncertainty in measurements of the instrument by the imaging system; and a target measurement model to compute a probability density function for the target to represent uncertainty in measurements of the instrument by the imaging system;

estimating an expected belief of system state for a subsequent time step based on the estimated given belief of system state and based on the corresponding measurement and the motion models computed over a plurality of different control inputs parameters for at least one of the imaging system and the intervention system;

computing information metrics for each of the expected belief of system states estimated for the subsequent time step; and selecting the control input parameters to control the at least one of the imaging system and the intervention system for the subsequent time step based on the computed information metrics.

14. A method comprising:

acquiring image data from an imaging system for a given time step, the image data representing at least one of an instrument and a target within an image space that includes patient anatomy, the imaging system and an intervention system operating according to control input parameters;

estimating a given belief of system state for the given time step, the given belief of system state for the given time step including an estimate of instrument state and target state determined from corresponding measurement and motion models computed based on the acquired image data and the control input parameters for the given time step, wherein the corresponding motion model comprises:

an instrument motion model to compute a probability density function for the instrument to represent uncertainty in estimating motion of the instrument; and a target motion model to compute a probability density function for the target to represent uncertainty in estimating the motions of the target;

estimating an expected belief of system state for a subsequent time step based on the estimated given belief of system state and based on the corresponding measurement and the motion models computed over a plurality of different control inputs parameters for at least one of the imaging system and the intervention system;

computing information metrics for each of the expected belief of system states estimated for the subsequent time step; and selecting the control input parameters to control the at least one of the imaging system and the intervention system for the subsequent time step based on the computed information metrics.

15. A system, comprising:

an imaging system to provide image data representing at least a portion of an image space, the image space including at least one of a device and a target within a patient's body;

an intervention system comprising intervention controls to control an intervention of the device with respect to the target within the patient's body; and a controller comprising a non-transitory memory storing instructions for an active localization method and a processor to execute the active localization method, the active localization method comprises:

estimating a given belief of system state for a given time step, including estimated beliefs of device state and target state, determined from corresponding measurement and motion models computed based on the image data and control input parameters for the given time step;

estimating expected beliefs of system state for a subsequent time step based on the estimated given belief of system state and based on the measurement models and the motion models computed over a plurality of different control inputs parameters for at least one of the imaging system and the intervention system; and selecting the control input parameters to actively control the at least one of the imaging system and the intervention system for the subsequent time step according to which of the control input parameters sufficiently maximize an information metric for the subsequent time step based on the expected beliefs of system state, wherein the device comprises a catheter comprising a plurality of multi-axial coils disposed about an elongated body of the catheter and the intervention controls further comprise robotic motion controls that actively control the catheter within the patient's body and actively control application of electrical current to the coils concurrently with application of a magnetic field provided by the imaging system.

16. The system of claim 15, wherein the intervention controls further comprise motion controls that employ Jacobian or inverse kinematics to control at least one state of the device.

17. The system of claim 15, wherein the active localization method further comprises a Bayes filter function to compute at the given belief of system state and the expected beliefs of system state for the subsequent time step.

18. The system of claim 17, wherein the Bayes filter function comprises one of a particle filter function and a Kalman filter function.

19. A system, comprising:

a catheter comprising a plurality of coil sets of multi-axial coils disposed about an elongated body of the catheter, at least two of the coil sets including multiple orthogonal coils;

a motion control system that employs inverse kinematics and/or Jacobian-based controls to control at least one state of the catheter, the motion control system comprising:

motion planning control comprising non-transitory memory that stores instructions and one or more processors to execute the instructions to determine control parameters for adjusting at least one of a position or orientation of the catheter in a three-dimensional coordinate system; and steering control, which is electrically connected with each of the coil sets, the steering control controlling application of electrical current to each of the coil sets to adjust a position of the catheter in the three-dimensional coordinate system based on the control parameters;

an imaging system to provide image data representing at least a portion of an image space, the image space including at least a portion of the catheter that includes the plurality of coil sets, the steering control to apply the current to the coils concurrently with application of a magnetic field from the imaging system to the image space to adjust the position of the catheter in the three-dimensional coordinate system according to the magnetic field and the current an active localization method executable by the one or more processors, the active localization method programmed to:

estimate a given belief of system state for a given time step, including estimated beliefs of device state for the catheter and target state of a target site, determined from corresponding measurement and motion models computed based on the image data and the control parameters for the given time step;

estimate expected beliefs of system state for a subsequent time step based on the estimated given belief of system state and based on the measurement models and the motion models computed over a plurality of different control inputs parameters for at least one of the imaging system and the intervention system; and select the control parameters to actively control the at least one of the imaging system and the motion control system for the subsequent time step according to which of the control input parameters sufficiently maximize an information metric for the subsequent time step based on the expected beliefs of system state.

20. One or more non-transitory computer readable media storing instructions that upon execution execute a method, the method comprising:

acquiring image data from an imaging system for a given time step, the image data representing at least one of an instrument and a target within an image space that includes patient anatomy, the imaging system and an intervention system operating according to control input parameters;

estimating a given belief of system state for the given time step, the given belief of system state for the given time step including an estimate of instrument state and target state determined from corresponding measurement and motion models computed based on the acquired image data and the control input parameters for the given time step, wherein the estimating the given belief of system state comprises using a Bayes filter function to compute the given belief of system state, the Bayes filter function comprises at least one of a particle filter to estimate a posterior density representing the given belief of system state or a Kalman filter function to estimate a mean and a covariance matrix representing the given belief of system state;

estimating an expected belief of system state for a subsequent time step based on the estimated given belief of system state and based on the corresponding measurement and the motion models computed over a plurality of different control inputs parameters for at least one of the imaging system and the intervention system;

computing information metrics for each of the expected belief of system states estimated for the subsequent time step; and selecting the control input parameters to control the at least one of the imaging system and the intervention system for the subsequent time step based on the computed information metrics.

21. One or more non-transitory computer readable media storing instructions that upon execution execute a method, the method comprising:

acquiring image data from an imaging system for a given time step, the image data representing at least one of an instrument and a target within an image space that includes patient anatomy, the imaging system and an intervention system operating according to control input parameters;

estimating a given belief of system state for the given time step, the given belief of system state for the given time step including an estimate of instrument state and target state determined from corresponding measurement and motion models computed based on the acquired image data and the control input parameters for the given time step, wherein the corresponding measurement model comprises:

an instrument measurement model to compute a probability density function for the instrument to represent uncertainty in measurements of the instrument by the imaging system; and a target measurement model to compute a probability density function for the target to represent uncertainty in measurements of the instrument by the imaging system; or wherein the corresponding motion model comprises:

an instrument motion model to compute a probability density function for the instrument to represent uncertainty in estimating motion of the instrument; and a target motion model to compute a probability density function for the target to represent uncertainty in estimating the motions of the target;

estimating an expected belief of system state for a subsequent time step based on the estimated given belief of system state and based on the corresponding measurement and the motion models computed over a plurality of different control inputs parameters for at least one of the imaging system and the intervention system;

computing information metrics for each of the expected belief of system states estimated for the subsequent time step; and selecting the control input parameters to control the at least one of the imaging system and the intervention system for the subsequent time step based on the computed information metrics.

* * * * *